United States Patent [19]

Hoki et al.

[11] Patent Number: 4,797,939
[45] Date of Patent: Jan. 10, 1989

[54] PATTERN MASKING METHOD AND AN APPARATUS THEREFOR

[75] Inventors: Tetsuo Hoki; Tetsuo Sano; Ryuji Kitakado, all of Kyoto; Yoshinori Sezaki, Itami; Tomiji Hotta; Hironobu Yano, both of Kyoto, all of Japan

[73] Assignee: Dainippon Screen Mfg. Co., Ltd., Kyoto, Japan

[21] Appl. No.: 914,863

[22] Filed: Oct. 2, 1986

[30] Foreign Application Priority Data

Oct. 4, 1985 [JP] Japan .................... 60-222454
Jul. 5, 1986 [JP] Japan .................... 61-158458

[51] Int. Cl.⁴ .................................... G06K 9/00
[52] U.S. Cl. .................................... 382/8; 356/237; 358/106; 358/107; 382/48
[58] Field of Search ............... 382/48, 8; 358/93, 106, 358/107

[56] References Cited

U.S. PATENT DOCUMENTS

| 3,882,463 | 5/1975 | Britt | 382/33 |
| 4,027,284 | 5/1977 | Hoshino et al. | 382/33 |
| 4,379,308 | 4/1983 | Kosmowski et al. | 358/106 |
| 4,486,777 | 12/1984 | Yamamura | 358/106 |
| 4,510,617 | 4/1985 | Mori | 382/33 |
| 4,545,070 | 10/1985 | Miyagawa et al. | 382/48 |
| 4,555,798 | 11/1985 | Broadbent, Jr. et al. | 358/106 |
| 4,560,273 | 12/1985 | Ando et al. | 356/237 |
| 4,596,037 | 6/1986 | Bouchard et al. | 382/8 |
| 4,644,583 | 2/1987 | Watanabe et al. | 358/107 |

Primary Examiner—Leo H. Boudreau
Attorney, Agent, or Firm—Lowe, Price, LeBlanc, Becker & Shur

[57] ABSTRACT

A binarized image data group of an inspected object for a plurality of pixels arrayed in the sub-scanning direction is sequentially created in order along the main scanning direction to determine whether or not the pattern of an inputted image corresponds to a standard through-hole pattern on the basis of the binarized image data group. When the determination is of yes, through-hole diameter masking data are sequentially created in order along the main scanning direction to sequentially perform masking processing on the binarized image data group of the inspected object arrayed in the sub-scanning direction. Thus, the through-hole pattern is automatically detected to be subjected to masking processing, whereby an inspected object having through-holes can be inspected by a pattern matching method.

9 Claims, 32 Drawing Sheets

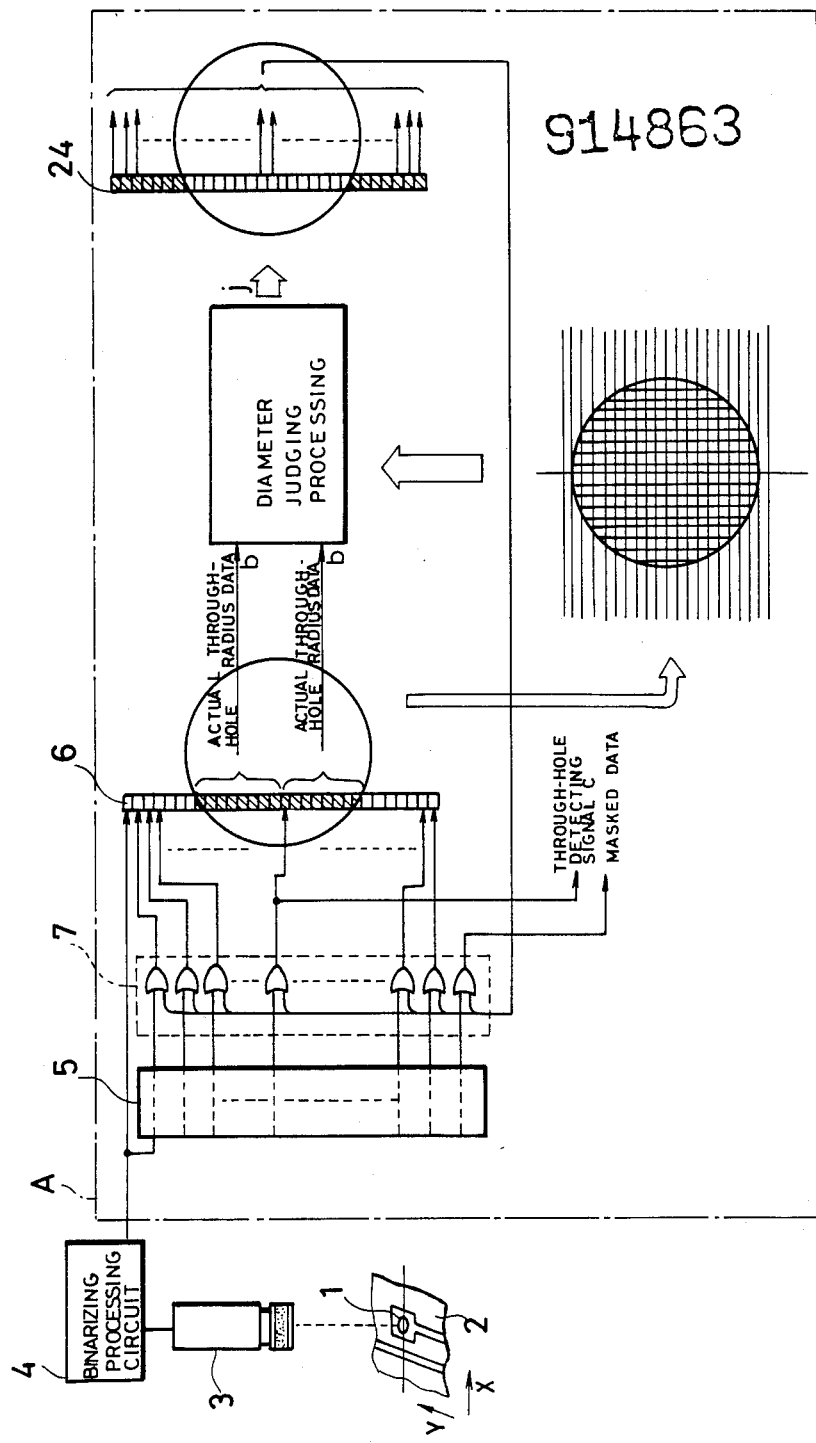

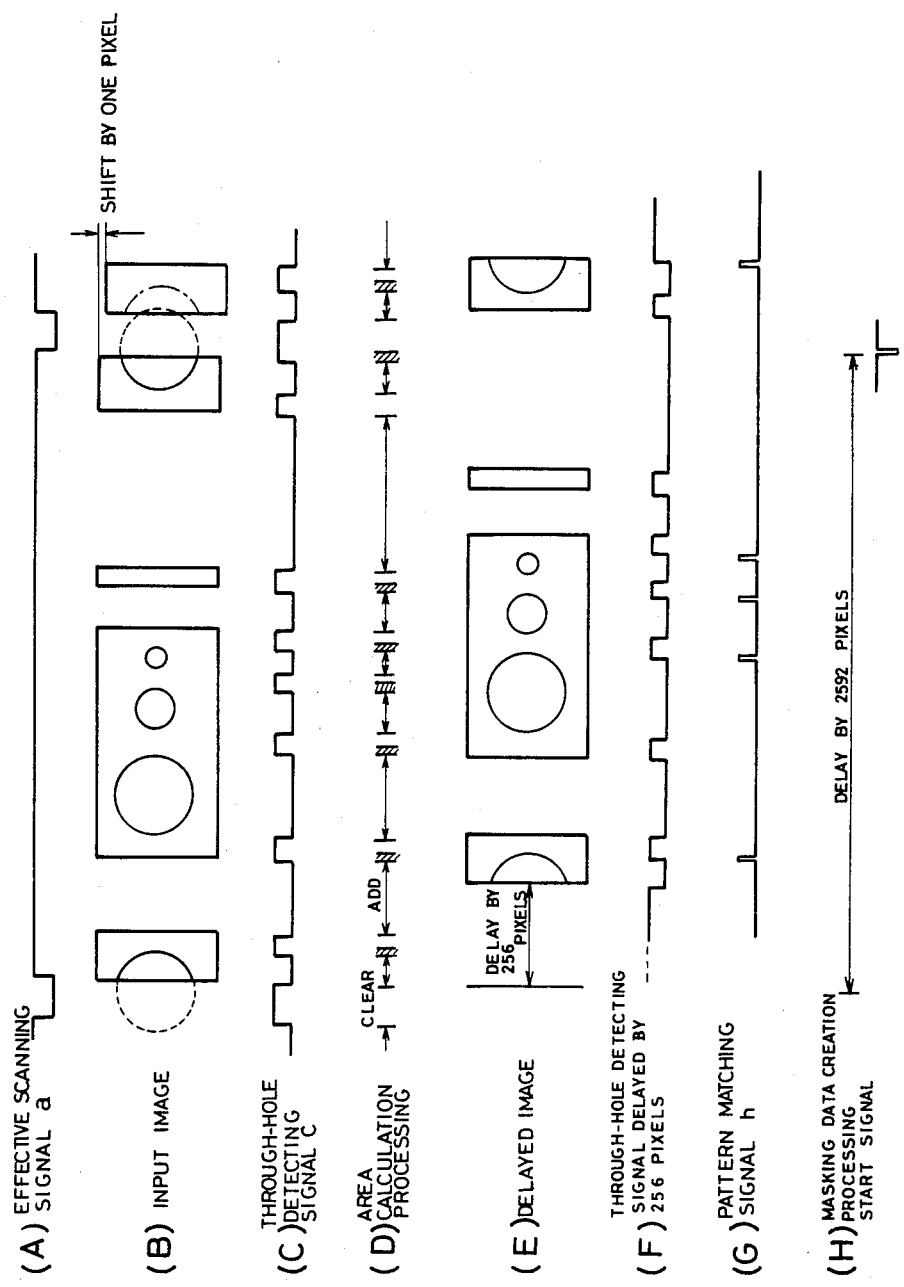

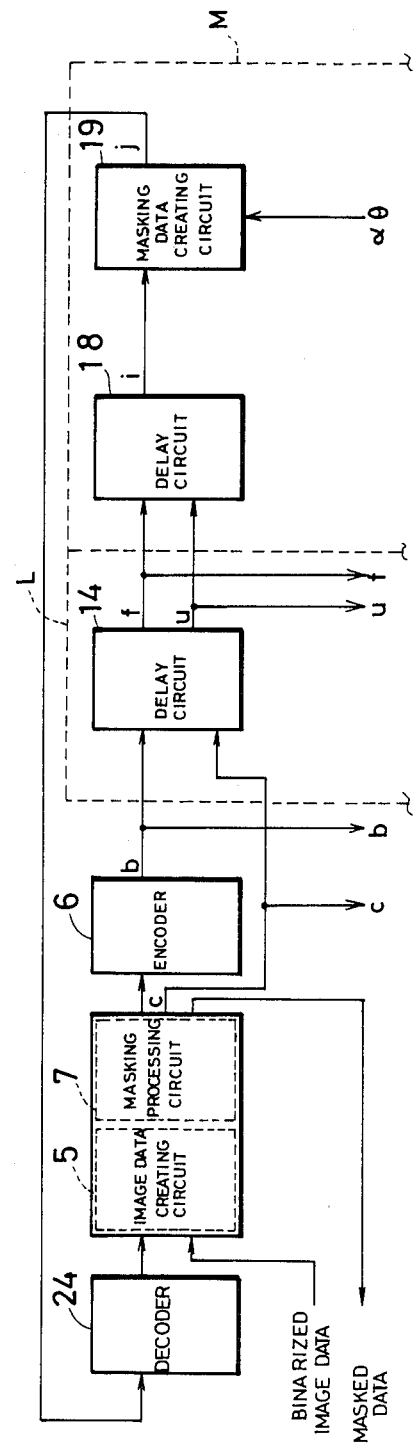

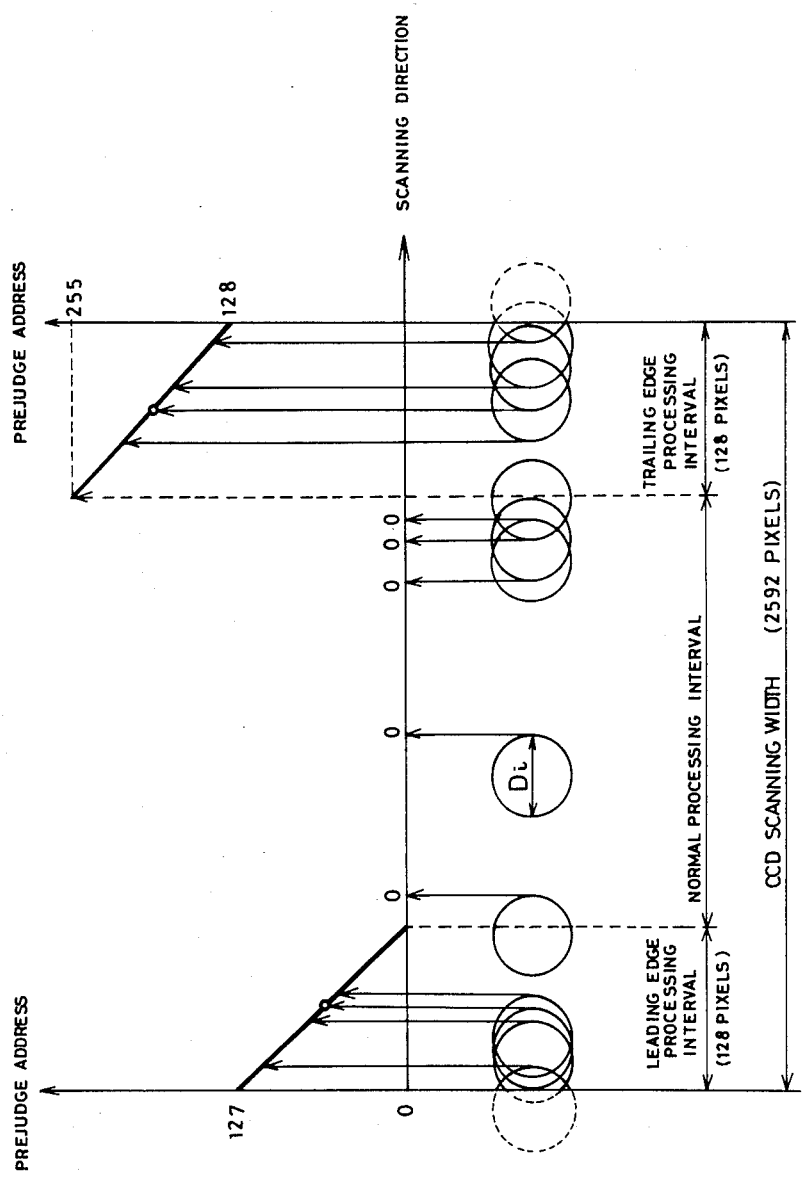

FIG. 5

| ADDRESS | | | | | | | | | | | | | ADDRESS | DATA | | | | | | | | | | | | | | | | |
|---|---|---|---|---|---|---|---|---|---|---|---|---|---|---|---|---|---|---|---|---|---|---|---|---|---|---|---|---|---|---|---|
| 12 | 11 | 10 | 9 | 8 | 7 | 6 | 5 | 4 | 3 | 2 | 1 | 0 | Hex. | 15 | 14 | 13 | 12 | 11 | 10 | 9 | 8 | 7 | 6 | 5 | 4 | 3 | 2 | 1 | 0 |
| 0 | 0 | 0 | 0 | 0 | X | X | X | X | X | X | X | X | 0 0 X | | | | | | | | | | | | | | | | |
| 0 | 0 | 0 | 0 | 1 | X | X | X | X | X | X | X | X | 0 1 X | across: AREA VALUE DATA (MINIMUM ALLOWABLE AREA OF THROUGH-HOLE / MAXIMUM SIZE THROUGH-HOLE / MAXIMUM ALLOWABLE AREA OF / MAXIMUM SIZE THROUGH-HOLE) | | | | | | | | | | | | | | | |
| ~ | | | | | | | | | | | | | ~ | | | | | | | | | | | | | | | | |
| 0 | 1 | 1 | 1 | 0 | X | X | X | X | X | X | X | X | 0 E X | | | | | | | | | | | | | | | | |
| 0 | 1 | 1 | 1 | 1 | X | X | X | X | X | X | X | X | 0 F X | | | | | | | | | | | | | | | | |
| 1 | 0 | 1 | 1 | 1 | X | X | X | X | X | X | X | X | 1 7 X | X | X | X | X | 0 | 0 | 0 | 0 | JUMPED ADDRESS DATA | | | | | | | |
| 1 | 1 | 0 | 0 | 0 | X | X | X | X | X | X | X | X | 1 8 X | | | | | | | | | | | | | | | | |
| 1 | 1 | 0 | 0 | 1 | X | X | X | X | X | X | X | X | 1 9 | | | | | | | | | | | | | | | | |
| 1 | 1 | 0 | 1 | 0 | | | | | | | | | 1 A | | | | | | | | | | | | | | | | |
| 1 | 1 | 0 | 1 | 1 | | | | | | | | | 1 B | | | | | | | | | | | | | | | | |
| 1 | 1 | 1 | 0 | 0 | | | | | | | | | 1 C | | | | | | | | | | | | | | | | |
| 1 | 1 | 1 | 0 | 1 | | | | | | | | | 1 D | | | | | | | | | | | | | | | | |
| 1 | 1 | 1 | 1 | 0 | X | X | X | X | X | X | X | X | 1 E X | | | | | | | | | | | | | | | | |
| 1 | 1 | 1 | 1 | 1 | X | X | X | X | X | X | X | X | 1 F X | X | X | X | X | | | | | | | | | | | | |

TYPE ADDRESS / MICRO ADDRESS / PREJUDGE ADDRESS

FIG. 6

| ADDRESS | | | |
|---|---|---|---|
| 12 | 11 10 9 8 | 7 6 5 4 3 2 1 0 | |
| D-C FLAG | MICRO ADDRESS (Hex) | PREJUDGE ADDRESS | CONTENT OF AREA VALUE DATA |
| 0 | (F) 15 | 0 | ※ |
| | | ⟨ | $S_{1max}$ |
| | | $127 - D_{1max}$ | $S_{1max}$ |
| | | $127 - D_{1max} + 1$ | $S_{1max}$ − (LEFT 1 PIXEL TRAIN AREA) |
| | | $127 - D_{1max} + 2$ | $S_{1max}$ − (LEFT 2 PIXEL TRAIN AREA) |
| | | $127 - D_{1max} + 3$ | $S_{1max}$ − (LEFT 3 PIXEL TRAIN AREA) |
| | | ⋮ | |
| | | $127 - D_{1max} + n$ | $S_{1max}$ − (LEFT n PIXEL TRAIN AREA) |
| | | ⋮ | ⋮ |
| | | 126 | RIGHT 2 PIXEL TRAIN AREA |
| | | 127 | RIGHT 1 PIXEL TRAIN AREA |
| | | 128 | RIGHT 1 PIXEL TRAIN AREA |
| | | 129 | RIGHT 2 PIXEL TRAIN AREA |
| | | 130 | RIGHT 3 PIXEL TRAIN AREA |
| | | 131 | RIGHT 4 PIXEL TRAIN AREA |
| | | ⋮ | ⋮ |
| | | $128 + D_{1max} - 1$ | $S_{1max}$ − (LEFT 1 PIXEL TRAIN AREA) |
| | | $128 + D_{1max}$ | $S_{1max}$ |
| | | ⋮ | $S_{1max}$ |
| | | 254 | $S_{1max}$ |
| | | 255 | $S_{1max}$ |
| | (E) 14 | 0 ⟨ 255 | AREA PIXEL NUMBER ($S_{1min}$) CORRESPONDING TO MINIMUM ALLOWABLE DIAMETER ($D_{1min}$) OF MINIMUM SIZE THROUGH-HOLE (RESPECTIVE VALUES OBTAIN BY REPLACING $D_{1max}$ BY $D_{1min}$ AND $S_{1max}$ BY $S_{1min}$ IN DATA AND ADDRESSES CORRESPONDING TO MICRO ADDRESS 15) |
| | (D) 13 | 0 ⟨ 255 | COMPARISON AREA DATA OF SECOND SMALLEST SIZE |
| | (C) 12 | 0 ⟨ 255 | |
| | ⋮ | ⋮ | ⋮ |
| | 16−2n+1 | 0 ⟨ 255 | COMPARISON AREA DATA OF MAXIMUM SIZE THROUGH-HOLE |
| | 16−2n | 0 ⟨ 255 | |

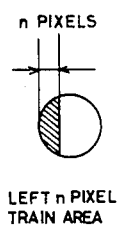

LEFT n PIXEL TRAIN AREA n PIXELS

※ PIXEL NUMBER ($S_{1max}$) OF AREA CORRESPONDING TO MAXIMUM ALLOWABLE DIAMETER ($D_{1max}$) OF MINIMUM SIZE THROUGH-HOLE

FIG. 7

| ADDRESS | | | DATA | | |
|---|---|---|---|---|---|
| 12 | 11 10 9 8 | 7 6 5 4 3 2 1 0 | 15 14 13 12 | 11 10 9 8 | 7 6 5 4 3 2 1 0 |
| DC-FLAG | TYPE ADDRESS | PREJUDGE ADDRESS | | CONTENT | |
| 1 | 7 | 0 | | | 0 |
| | | ⟨ | | | 0 |
| | | 255 | | | 0 |
| | 8 | 0 | X | 8 | 0 |
| | | ⟨ | | | 0 |
| | | 127−$D_1$ | | | 0 |
| | | 127−$D_1$+1 | | | 1 |
| | | 127−$D_1$+2 | | | 2 |
| | | ⋮ | | | ⋮ |
| | | 126 | | | $D_1$−1 |
| | | 127 | | | $D_1$ |
| | | 128 | | | 0 |
| | | ⟨ | | | 0 |
| | | 255 | | | 0 |
| | 9 | 0 | | 9 | 0 |
| | | ⟨ | | | 0 |
| | | 127−$D_2$ | | | 0 |
| | | 127−$D_2$+1 | | | 1 |
| | | 127−$D_2$+2 | | | 2 |
| | | ⋮ | | | ⋮ |
| | | 126 | | | $D_2$−1 |
| | | 127 | | | $D_2$ |
| | | 128 | | | 0 |
| | | ⟨ | | | 0 |
| | | 255 | | | 0 |
| | ⋮ | | | ⋮ | |
| | 7+n | 0 | | 7+n | 0 |
| | | ⟨ | | | 0 |
| | | 127−$D_n$ | | | 0 |
| | | 127−$D_n$+1 | | | 1 |
| | | 127−$D_n$+2 | | | 2 |
| | | 127−$D_n$+3 | | | 3 |
| | | ⋮ | | | ⋮ |
| | | 126 | | | $D_n$−1 |
| | | 127 | | | $D_n$ |
| | | 128 | | | 0 |
| | | ⟨ | | | 0 |
| | | 255 | | | 0 |

| 15 | END ZONE DATA |
| 14 | |
| 13 | |
| 12 | SHIFT DATA |
| 11 | |
| 10 | |
| 9 | |
| 8 | |
| 7 | MAXIMUM ALLOWABLE |
| 6 | RADIUS DATA |
| 5 | |
| 4 | |
| 3 | |
| 2 | MINIMUM ALLOWABLE |
| 1 | RADIUS DATA |
| 0 | |

FIG. 13

| ADDRESS | | DATA | | |
|---|---|---|---|---|
| 11 10 9 8 \| 7 6 5 4 3 2 1 0 | 15 | 14 13 12 11 10 9 8 7 6 5 | 4 3 2 1 0 | |
| 0 | 0 | 0 | 0 | 0 |
| 8 \| 0 | 0 | $L_1$ | $Y_1 max(0)$ | 0 |
| 1 | | | $Y_1 max(1)$ | 0 |
| 2 | | | $Y_1 max(2)$ | 0 |
| ⋮ | | | ⋮ | ⋮ |
| $d_1-1$ | | | $Y_1 max(d_1-1)$ | 0 |
| $d_1$ | | | $Y_1 max(d_1)$ | $Y_1 min(d_1)$ |
| $d_1+1$ | | | $Y_1 max(d_1+1)$ | $Y_1 min(d_1+1)$ |
| ⋮ | | | ⋮ | ⋮ |
| $D_1min + d_1-1$ | 0 | | $Y_1 max(A_7-0)$ | $Y_1 min(A_7-0)$ |
| $D_1min + d_1$ | 1 | | $Y_1 max(A_7-0)$ | 0 |
| $D_1min + d_1+1$ | 1 | | $Y_1 max(A_7-0)$ | 0 |
| ⋮ | | | ⋮ | |
| $D_1max - d_1-1$ | 1 | | $Y_1 max(A_7-0)$ | 0 |
| $D_1max - d_1$ | 0 | | 0 | 0 |
| $D_1max - d_1+1$ | 0 | | 0 | 0 |
| ⋮ | | | ⋮ | ⋮ |
| 255 | 0 | | 0 | 0 |
| 9 \| 0 | 0 | $L_2$ | $Y_2 max(0)$ | 0 |
| 1 | | | $Y_2 max(1)$ | 0 |
| 2 | | | | |
| ⋮ | | | | |
| 7+n \| 0 | 0 | $L_n$ | $Y_n max(0)$ | 0 |
| 1 | | | $Y_n max(1)$ | 0 |
| 2 | | | $Y_n max(2)$ | 0 |
| ⋮ | | | | |
| $d_n-1$ | | | $Y_n max(d_n-1)$ | 0 |
| $d_n$ | | | $Y_n max(d_n)$ | $Y_1 min(d_n)$ |
| $d_n+1$ | | | $Y_n max(d_n+1)$ | $Y_1 min(d_n+1)$ |
| ⋮ | | | ⋮ | |
| $D_n min + d_n-1$ | 0 | | $Y_n max(A_7-0)$ | $Y_1 min(A_7-0)$ |
| $D_n min + d_n$ | 1 | | $Y_n max(A_7-0)$ | 0 |
| $D_n min + d_n+1$ | 1 | | $Y_n max(A_7-0)$ | 0 |
| ⋮ | | | ⋮ | |
| $D_n max - d_n-1$ | 1 | | $Y_n max(A_7-0)$ | 0 |
| $D_n max - d_n$ | 0 | | 0 | 0 |
| $D_n max - d_n+1$ | 0 | | 0 | 0 |
| ⋮ | | | | |
| 255 | 0 | | 0 | 0 |

※ $A_7-0$: VALUES OF LOWER 8 BITS OF ADDRESSES

FIG. 15
| | CONTENT |
|---|---|
| 7 | MASKING TERMINATION FLAG $\beta$ |
| 6 | MASKING FUNCTION DATA $\alpha$ |
| 5 | |
| 4 | |
| 3 | MASKING DATA $\theta$ |
| 2 | |
| 1 | |
| 0 | |
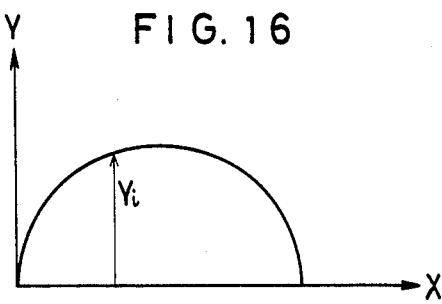
FIG. 16
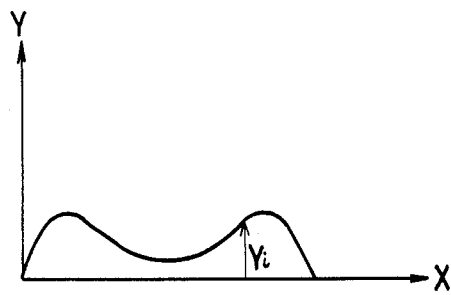
FIG. 17(A)
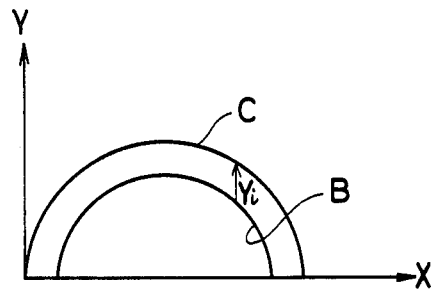
FIG. 17(B)

FIG. 18

| ADDRESS ($\omega$) | | DATA ($\beta \alpha \theta$) | | |
|---|---|---|---|---|
| 11 10 9 8 | 7 6 5 4 3 2 1 0 | 7 6 5 | 4 3 2 1 0 | REMARK |
| 0 | | | 0 | PROCESSING IV |
| 8 | 0 | 1 1 1 | X X X X X | |
| | 1 | 1 1 1 | | |
| | . | . . . | | PROCESSING I |
| | . | . . . | | |
| | 127 | 1 1 1 | X X X X X | |
| 9 | 0 | 1 0 1 | $Y_2(0)$ | |
| | 1 | 1 | $Y_2(1)$ | |
| | 2 | 1 | $Y_2(2)$ | |
| | 3 | 1 | | |
| | 4 | 1 | | |
| | 5 | 1 | | |
| | 6 | 1 | | |
| | . | . | . | PROCESSING III |
| | . | . | . | |
| | k | 1 | $Y_2(k)$ | |
| | . | . | . | |
| | $\ell$ | 1 | $Y_2(\ell)$ | |
| | $\ell+1$ | 0 | 0 | |
| | $\ell+2$ | 0 | 0 | |
| | . | . | . | |
| | 127 | 0 0 1 | 0 | |
| 10 | 0 | 1 1 0 | $Y_3(0)$ | |
| | 1 | 1 | $Y_3(1)$ | |
| | 2 | 1 | $Y_3(2)$ | |
| | 3 | 1 | . | |
| | . | . | . | |
| | k' | 1 | $Y_3(k')$ | PROCESSING II |
| | . | . | . | |
| | $\ell'$ | 1 | $Y_3(\ell')$ | |
| | $\ell'+1$ | 0 | 0 | |
| | . | . | . | |
| | 127 | 0 1 0 | 0 | |

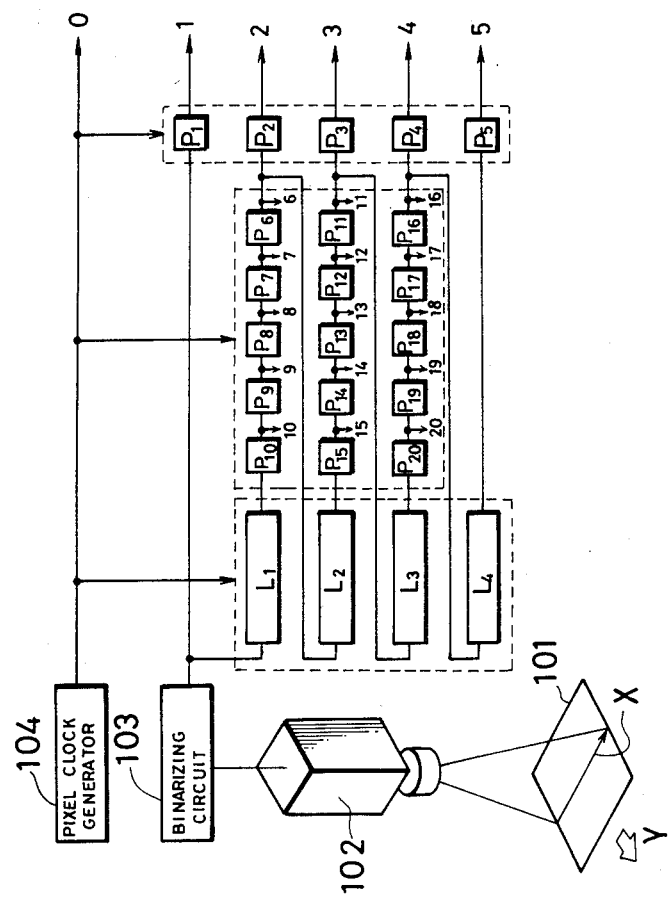

FIG. 23
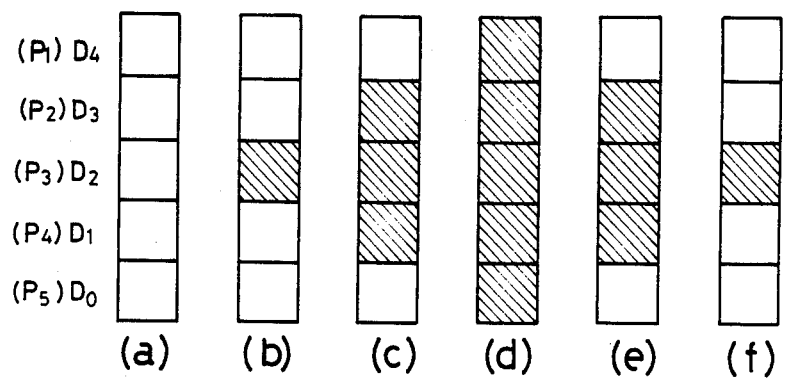
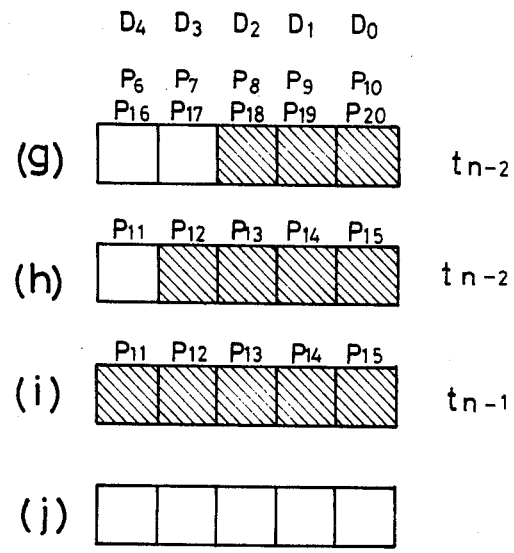

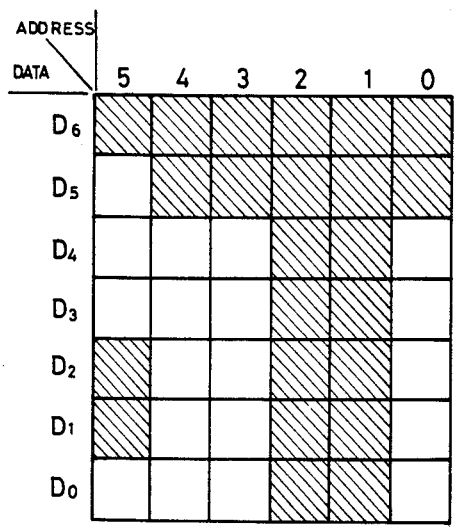

| DATA \ ADDRESS | 5 | 4 | 3 | 2 | 1 | 0 |
|---|---|---|---|---|---|---|
| $D_4$ |   |   |   |   | ▨ | ▨ |
| $D_3$ |   |   |   |   | ▨ | ▨ |
| $D_2$ |   |   |   |   |   |   |
| $D_1$ |   |   |   |   |   |   |
| $D_0$ |   |   |   |   |   |   |

PATTERN MASKING METHOD AND AN APPARATUS THEREFOR

BACKGROUND OF THE INVENTION

1. Field of the Invention

The present invention relates to a pattern masking method and an apparatus therefor employed for pattern defect inspection, and more particularly, it relates to a pattern masking method and an apparatus therefor employed for inspecting printed wiring boards having through-holes.

2. Description of the Prior Art

In pattern defect inspection of printed wiring boards or the like, pattern defects are mainly detected through a pattern matching method and a feature extraction method nowadays. In the former method, image patterns of inspected objects are overlapped with the image pattern of a reference object to be compared with the same, thereby to judge that mismatched parts are defective (for example, refer to Japanese Patent Publication Gazette No. 2069/1984 and Japanese Patent Laying-Open Gazette No. 61604/1985. In the latter method, various features such as line width, angle, specific pattern etc. included in a reference image pattern are stored so that, when a pattern belonging to none of the said features is detected in an inspected image, the said pattern is judged to be defective (for example, refer to Japanese Patent Laying-Open Gazette No. 149905/1982).

In the pattern defect detection through the said pattern matching, however, a problem is caused in defect detection of printed wiring boards having through-holes such as those of double-layer structure, although no such problem is caused in defect detection of printed wiring boards having no through-holes such as inner layer wiring boards provided on inner layers of multilayer structure. In case of the printed wiring boards having through-holes, positions of the through-holes are generally varied by about 100 $\mu$m with misregistration in set positions of the printed wiring boards and that of drill edges in formation of the through-holes. Misregistration of the through-holes causes no practical problem in such a range of variation. However, when image patterns of inspected objects are overlapped with that of a reference object for comparison, the patterns are mismatched at the through-hole positions, whereby the said positions are judged to be defective even if land patterns and lead wire patterns are matched with each other. Thus, pattern defects of the printed wiring boards having through-holes cannot be correctly detected by the conventional pattern matching method and the defects must be visually detected after formation of the through-holes, whereby pattern defect detection is extremely complicated and detection accuracy is varied with inspectors.

SUMMARY OF THE INVENTION

The present invention is directed to a pattern masking method and an apparatus therefor applicable, which are applicable to inspection of printed wiring boards having through-holes.

According to the pattern masking method of the present invention, binarized image data of an inspected object having through-holes are inputted in a time-series manner along the main scanning direction, to sequentially create a binarized image data group for a plurality of pixels arrayed in the subscanning direction (image data creating step). Then, on the basis of the sequentially created binarized image data group, a determination is made as to whether or not the pattern of an inputted image corresponds to a standard through-hole pattern (pattern judging step). When the pattern of the inspected image is judged to correspond to the standard through-hole pattern, through-hole diameter masking data are sequentially created in the main scanning direction (masking data creating step). On the basis of the through-hole diameter masking data thus created, the binarized image data group of the inspected object arrayed in the sub-scanning direction are sequentially subjected to masking processing (masking processing step).

The pattern masking apparatus according to the present invention is adapted to carry out the aforementioned pattern masking method, and comprises means respectively corresponding to the image data creating step, the pattern judging step, the masking data creating step and the masking processing step of the pattern masking method, i.e., image data creating means, pattern judging means, masking data creating means and masking processing means.

Accordingly, a principal object of the present invention is to provide a pattern masking method and an apparatus therefor for automatically detecting through-hole patterns to mask the same, thereby to enable inspection of objects having through-holes by a pattern matching method.

According to the present invention, a group of binarized image data for a plurality of pixels arrayed in a subscanning direction are sequentially created in order along the main scanning direction to judge whether or not the pattern of an inputted image corresponds to the standard through-hole pattern on the basis of the binarized image data group. If the determination is of yes, through-hole diameter masking data are sequentially created in order along the main scanning direction to sequentially perform masking processing on the binarized image data group of the inspected object arrayed in the subscanning direction. The through-hole pattern is thus automatically detected to be subjected to masking processing, whereby inspection through the pattern matching method is performed in a state similar to the case where no through-hole is provided by inspecting the object by the pattern matching method through the binarized image data after masking processing. Thus, an inspected object having through-holes can be correctly inspected by the pattern matching method with no influence by position accuracy of the through-holes.

These and other objects, features, aspects and advantages of the present invention will become more apparent from the following detained description of the present invention when taken in conjunction with the accompanying drawings.

BRIEF DESCRIPTION OF THE DRAWINGS

FIG. 1 conceptually illustrates the masking principle of a first embodiment of the present invention;

FIG. 2 is a timing chart showing masking procedure thereof;

FIG. 4 is a diagram for illustrating mapping of pre-judge addresses with respect to CCD scanning width;

FIG. 5 schematically illustrates the content of a prejudge memory;

FIG. 6 partially illustrates area value data of the prejudge memory in detail;

FIG. 7 partially illustrates jumped address data of the prejudge memory in detail;

FIG. 13 is a diagram for illustrating the pattern data memory in detail;

FIG. 15 illustrates data structure of a masking data memory;

FIG. 16 is a diagram for illustrating the content of the masking data memory corresponding to masking processing II;

FIG. 17 A and B is a diagram for illustrating the content of the masking data memory corresponding to masking processing III;

FIG. 18 is a detailed explanatory diagram showing the masking data memory;

FIG. 23 illustrates data latched in flip-flops;

FIG. 31 illustrates memory data stored in a memory;

FIG. 32 A and B illustrates data latched in flip-flops;

DESCRIPTION OF THE PREFERRED EMBODIMENTS

(I) First Embodiment

Description is now made on a first embodiment of the present invention.

A. Principle of Pattern Masking

Figure 3B:
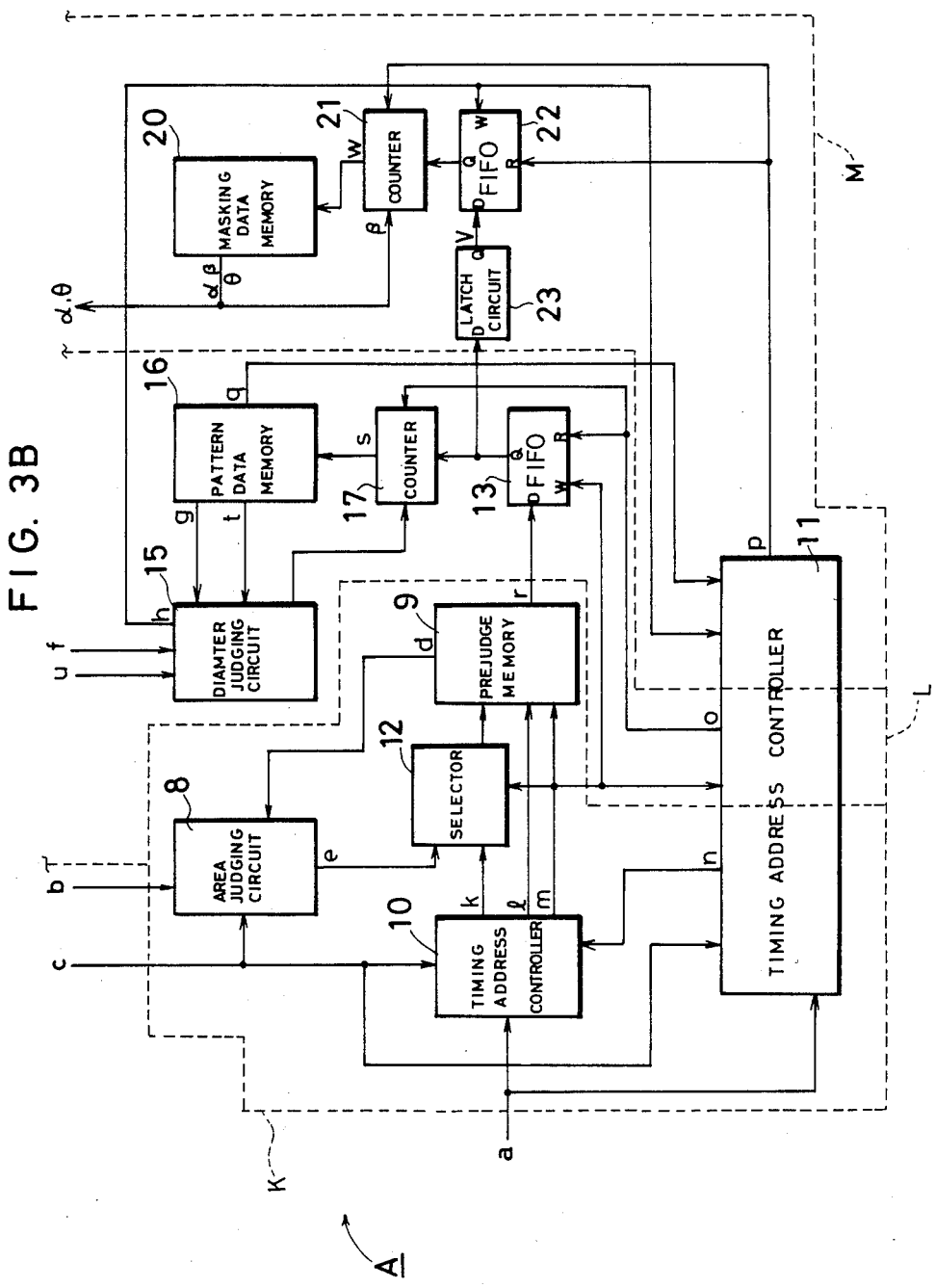
FIG. 3, consisting of FIGS. 3A and 3B, is a block diagram showing a pattern masking apparatus of a first embodiment.

In order to facilitate understanding of a pattern masking method and an apparatus therefor according to a first embodiment of the present invention, description is now made on the principle of through-hole pattern masking. FIG. 1 conceptually illustrates the masking principle, FIG. 2 is a timing chart showing masking procedure and FIG. 3 is a block diagram showing an example of the masking apparatus. The masking apparatus as shown in FIG. 3 is in correspondence to a definite embodiment as hereinafter described, and hence the said apparatus is only briefly described within a range required for explaining the principle, and details thereof are hereinafter described with reference to the definite embodiment.

1. Input of Image Data

Referring to FIG. 1, image data of an inspected object such as a printed wiring board 2 or the like having a through-hole 1 are inputted by moving the printed wiring board 2 at a constant speed in a direction Y (sub-scanning direction) while scanning a CCD line sensor 3 (line sensor of 2592 elements in this embodiment) in a direction X (main scanning direction). Analog image data thus obtained are binarized to digital image data through a binarizing processing circuit 4, to be inputted in an image data creating circuit 5 (see FIG. 3) of a pattern masking apparatus A in a time-series manner.

2. Creation of Binarized Image Data Arrayed in sub-Scanning Direction

In the image data creating circuit 5, delay processing for one scanning line (2592 elements + dummy element (blanking pixel number)) is sequentially performed on the inputted binarized image data for 63 lines, thereby to create a group of binarized image data arrayed in the sub-scanning direction for 64 pixels in total with binarized image data for one pixel before the delay processing. Such a binarized image data group is sequentially created every time new binarized image data are inputted in the image data creating circuit 5, to be outputted to a subsequent circuit. Thus, a binarized image of an inspected object is expanded to a two-dimensional image on time series through the image data creating circuit 5.

FIG. 2(B) typically shows the two-dimensional image of the inspected object pattern obtained by the aforementioned method. The horizontal direction of FIG. 2(B) corresponds to the main scanning direction and the vertical direction corresponds to the sub-scanning direction. Circled regions of FIG. 2(B) show through-hole patterns, and the through-hole image data are supplied by an "L" signal. Rectangular regions show land patterns or wiring patterns, and the image data are supplied by an "H" signal. Other regions correspond to those on a printed substrate surface provided with no land or wiring patterns, and the image data are supplied by an "L" signal similarly to the through-hole patterns. The respective signals may be inverted in polarity.

FIG. 2(A) shows an effective scanning signal a of the CCD line sensor 3, in which an "H" region corresponds to one main scanning (2592 elements) effective interval and an "L" region corresponds to a blanking interval.

3. Measurement of Through-Hole Diameter

With respect to the binarized image data group for 64 pixels arrayed in the sub-scanning direction created by the image data creating circuit 5 (FIG. 1) in the aforementioned manner, image data on the first pixel (image data not subjected to delay processing) are directly inputted in an encoder (through-hole diameter measuring means) 6 and the image data on the second to 64th pixels are inputted in the encoder 6 through a masking processing circuit 7 formed by a group of AND circuits. The function of the masking processing circuit 7 is hereinafter described in detail. It is assumed here that no masking processing is performed in the masking processing circuit 7, and "L" signals are supplied to all of input terminals of the respective AND circuits opposite to those receiving the aforementioned image data so that the binarized image data for 64 pixels arrayed in the sub-scanning direction are directly inputted in the encoder 6.

The encoder 6 is formed by an upper encoder for 32 pixels and a lower encoder for 32 pixels to be capable of detecting the size (hereinafter referred to as "through-hole diameter" in this specification) of the through-hole image in the sub-scanning direction separately in the upper and lower regions. The encoder 6 is adapted to detect the number of "L" signals continuous from a central pixel position (uppermost pixel position of the lower encoder in this embodiment) in the sub-scanning direction, i.e., the numbers of pixels corresponding to the through-hole diameters separately by the upper and lower encoders, to perform encoding in correspondence to the respective numbers of detected pixels and output the same as measured through-hole diameter data b.

On the other hand, a signal inputted in the central pixel position of the encoder 6 is independently fetched from an output terminal positioned at the center of the masking processing circuit 7 to serve as a through-hole detecting signal c. FIG. 2(C) shows the through-hole detecting signal c corresponding to the two-dimensional image as shown at FIG. 2(B). As obvious from FIG. 2(C), the through-hole detecting signal c goes high in the land pattern and wiring pattern regions and blanking intervals and goes low in other through-hole pattern regions and substrate surface regions.

4. Calculation of Through-Hole Area Value

When the aforementioned measured data of the through-hole are obtained, the through-hole areas are calculated on the basis of the measured data. The through-hole areas are calculated by an area judging circuit 8 as shown in FIG. 3. When the beginning end of a through-hole is detected on a trailing edge of the through-hole detecting signal c (see FIG. 2(C)), the measured through-hole diameter data b measured by the encoder 6 are read in the area judging circuit 8. When the through-hole detecting signal c is at an "L" level, i.e., when the through-hole image data are supplied to the encoder 6, the measured through-hole diameter data b measured by the encoder 6 are sequentially read in the area judging circuit 8 so that the values thereof are sequentially added in a cumulative manner. When the terminating end of the through-hole is detected on a leading edge of the through-hole detecting signal c, a pixel number corresponding to the through-hole area is obtained as a final value through cumulative addition.

The lower part of FIG. 1 typically shows the principle of obtaining the through-hole area by sequentially cumulatively adding measured through-hole diameters in order along the main scanning direction. Since the measured through-hole diameters are given in pixel numbers in this case, the through-hole area is obtained also in a pixel number. Arrow intervals as shown at FIG. 2(D) denote intervals for cumulatively adding the through-hole diameters, i.e., through-hole area calculating intervals.

5. Judgement of Through-Hole Area

When the through-hole area is calculated, the calculated through-hole area is compared with maximum and minimum allowable area values with respect to a standard through-hole, to judge whether or not the through-hole is of prescribed size. The data on the area value of the standard through-hole are stored in a prejudge memory 9 as shown in FIG. 3, and area value data d are sequentially read in the area judging circuit 8 by first data reading means formed by timing address controllers 10 and 11 and a selector 12. The area judging circuit 8 sequentially compares the calculated through-hole areas with the area value data d (maximum allowable area data and minimum allowable area data) read from the prejudge memory 9, to judge whether or not the through-holes are of prescribed size.

The results of judgement are supplied as timing address data e to the prejudge memory 9 through the selector 12. In addition to the aforementioned area value data, the prejudge memory 9 stores jumped address data mapped with type addresses. Therefore, when the aforementioned type address data e are supplied to the prejudge memory 9, jumped address data r mapped with the type addresses are read to be written in an FIFO 13 in a subsequent stage. The jumped address data are required for performing through-hole diameter comparison processing and through-hole diameter masking data creating processing thereafter, and correspond to addresses for starting data reading from a pattern data memory 16 and a masking data memory 20, as hereinafter described in detail.

Such area judging processing is performed in slanted intervals as shown at FIG. 2(D), i.e., immediately upon completion of every area calculation processing. The jumped address data thus obtained are sequentially stored in the FIFO 13 (FIG. 3).

The area judging circuit 8, the prejudge memory 9, the timing address controllers 10 and 11 and the selector 12 as shown in FIG. 3 form an area judging means K.

6. Judgement of Through-Hole Diameter

When the through-hole areas are judged, i.e., when the jumped addresses are determined, the respective measured through-hole diameters measured in order along the main scanning direction of the through-hole image are sequentially compared with the maximum allowable through-hole diameter and the minimum allowable through-hole diameter corresponding to respective positions, and determinations are made as to whether or not the same are included in an allowable range. Such through-hole diameter judging processing is performed by a diameter judging means L formed by a first delay circuit 14, a diameter judging circuit 15, a pattern data memory 16, a counter 17, the FIFO 13 and the timing address controller 11 as shown in FIG. 3.

In further detail, the measured through-hole diameter data b measured by the encoder 6 are delayed by prescribed pixels (256 pixels in this embodiment) by the first delay circuit 14 to be sequentially transmitted to the diameter judging circuit 15, in the form of a signal f as shown in FIG. 3. FIG. 2(E) shows a delayed image obtained by delaying the inputted image of FIG. 2(B) by 256 pixels.

On the other hand, the pattern data memory 16 stores through-hole diameter data (maximum allowable through-hole diameter data and minimum allowable through-hole diameter data) mapped with respected positions of the standard through-hole along main scanning lines in order of addresses, with the aforementioned jumped addresses as head addresses. The through-hole diameter data g are sequentially read in the diameter judging circuit 15 through a second data reading means formed by the timing address controller 11, the FIFO 13 and the counter 17 in synchronization with the delay in the first delay circuit 14.

The diameter judging circuit 15 sequentially compares the aforementioned measured through-hole diameter data f sequentially received in order along the main scanning direction with the aforementioned through-hole diameter data g (maximum and minimum allowable through-hole diameter data) read in order of addresses from the jumped addresses of the pattern data memory 9, to sequentially judge whether or not all of the actual through-hole diameters are included in the allowable range.

When all of the measured through-hole diameters are judged to be within the allowable range, the through-hole is regarded to correspond to that of the prescribed size to be masked, whereby the diameter judging circuit 15 outputs a pattern matching signal h. FIG. 2(F) shows a signal obtained by delaying the through-hole detecting signal c as shown at FIG. 2(C) by 256 pixels, and diameter judging processing is performed in "L" intervals of the said signal. FIG. 2(G) shows the pattern matching signal h, which goes high upon confirmation of pattern matching by the aforementioned diameter judging processing.

When, to the contrary, the measured through-hole diameters are out of the allowable range during the diameter judging processing, the inspected image is not a through-hole or the same is a defective through-hole which is not subjected to the masking processing, whereby no pattern matching signal h is outputted from the diameter judging circuit 15 at this time. Further description on this is made with reference to FIG. 2. For example, when an inspected image is directed to the surface of a substrate provided with no land pattern or wiring pattern, the area judging processing at FIG. 2(D) is performed similarly to the case of the through-hole while, even if the result of judgement is within the allowable area range set with respect to the standard through-hole and subsequent diameter judging processing is performed, the through-hole diameter inevitably comes out of the allowable range during the diameter judging processing, whereby no pattern matching signal h is outputted. Further, if a through-hole is partially defective in case of diameter judging processing with respect to a through-hole image, the through-hole diameter comes out of the allowable range in the defective portion, whereby no pattern matching signal h is outputted also in this case.

Although the above description is made on assumption that the pattern data memory 16 stores the through-hole diameter data (data on full length of the standard through-hole in the sub-scanning direction), the standard through-hole is in the form of a vertically symmetrical circle in practice, and hence the pattern data memory 16 stores diameter data for an upper region of the standard through-hole, i.e., through-hole radius data. The diameter judging circuit 15 separates the measured through-hole diameter of the encoder 6 in upper and lower regions as shown substantially at the central position (diameter judging processing) of the principle diagram of FIG. 1, to compare the same with the aforementioned through-hole radius data respectively, thereby to perform judgement on the through-hole diameters.

In this embodiment, a pattern discriminating means is formed by the encoder 6 (through-hole diameter measuring means), the area judging means K and the diameter judging means L.

7. Creation of Through-Hole Diameter Masking Data

When an inspected image is determined as the target through-hole in the aforementioned processing, through-hole diameter masking data for masking the through-hole image are sequentially created in order along the main scanning direction. The masking data creation processing is performed by a masking data creating means M formed by a second delay circuit 18, a masking data creating circuit 19, a masking data memory 20, a counter 21, a FIFO 22, a D-FF 23 and the timing address controller 11.

In further detail, the measured through-hole diameter data b measured by the encoder 6 are delayed by 256 pixels through the first delay circuit 14 and further delayed by prescribed pixels through the second delay circuit 18, to be sequentially transmitted to the masking data creating circuit 19 in a delay for one main scanning line (2592 pixels) in total, in the form of a signal i as shown in FIG. 3.

On the other hand, the masking data memory 20 stores data required for creation of the through-hole diameter masking data in order of addresses with the aforementioned jumped addresses as the head addresses, as hereinafter described in detail. These masking processing data are read in the masking data creating circuit 19 in synchronization with the delay in the second delay circuit 18 by a second data reading means formed by the timing address controller 11, the FIFO 22 and the counter 21.

The masking data creating circuit 19 sequentially creates through-hole diameter masking data (shown as signal j in FIG. 3) through use of the aforementioned through-hole diameter data i delayed by one scanning line (2592 pixels) and sequentially received therein and masking function data $\alpha$ and masking data $\theta$ sequentially read in order of addresses from the jumped addresses of the masking data memory 20 only with respect to an inspected image for which the pattern matching signal h is outputted. In this case, the through-hole diameter masking data j are obtained by encoding a number of pixels for a diameter identical to or slightly larger than the measured through-hole diameter.

8. Masking Processing

The through-hole diameter masking data j thus obtained are inputted in a decoder 24, which in turn performs decoding processing in correspondence to the encoding processing in the encoder 6. The right-hand region of FIG. 1 shows a binarized masking data group for 64 pixels decoded by the decoder 24 on the basis of the through-hole diameter masking data j. In the binarized masking data group, regions requiring masking processing are given by "H" signals and other regions are given by "L" signals. The central pixel position of the binarized masking data group deviates by one pixel in the sub-scanning direction from the central pixel position of the encoder 6 by the delay processing for one scanning line by the delay circuits 14 and 18.

The binarized maskinig data group is inputted in other side input terminals of the respective AND circuits of the masking processing circuit 7 as shown in FIG. 1 respectively. One-side input terminals of the AND circuits of the masking processing circuit 7 receive the binarized image data group delayed by one scanning line through the image data creating circuit 5 as hereinabove described, whereby the respective through-hole data of the "L" signals included in the binarized image data group are converted into "H" signals by AND processing with respective masking data of the H signals included in the binarized masking data group.

The binarized image data (masked data) obtained by masking processing of the through-hole pattern are outputted in a time-series manner from the AND circuit in·the last stage of the masking processing circuit 7, to be sequentially transmitted in a pattern defect detecting circuit (not shown) in a subsequent stage for pattern defect detecting processing.

The upper right-hand region of FIG. 2 conceptually shows masking processing of a through-hole image performed in a delay by one scanning line.

B. Application of Pattern Masking

The above description has been made on basic pattern masking processing, while the following functions are further added to this embodiment.

1. Masking Processing Responsive to Through-Hole Types

The above description has been made on assumption that a single type of through-hole is subjected to masking processing, while this embodiment is adapted to mask a plurality of types (eight types in this embodiment) of through-holes.

In more detail, the prejudge memory 9 stores respective maximum allowable area data and minimum allowable area data in correspondence to eight types of standard through-holes. These area data are sequentially read in the area judging circuit 8 to be compared with cumulatively added calculated through-hole area values. The through-holes are sorted by this comparison, so that the results are supplied as type address data e to the prejudge memory 9 through the selector 12. The prejudge memory 9 is provided with eight type addresses corresponding to the eight types of standard through-holes, to previously store jumped address data of the pattern data memory 16 and the masking data memory 20 in mapping with the respective type addresses. When the type address data e are supplied to the prejudge memory 9, jumped address data responsive to the results of sorting of the through-holes are read from the prejudge memory 9 to be written in the FIFO 13.

On the other hand, the pattern data memory 16 and the masking data memory 20 store data required for judging diameters of the eight types of through-holes and those required for masking the eight types of through-holes dividedly in prescribed regions, such that head addresses of respective regions are matched with the aforementioned jumped addresses. Therefore, data corresponding to the types of the through-holes are read from the pattern data memory 16 and the masking data memory 20 in diameter judging processing and masking data creating processing, to perform required diameter judging processing and masking data creating processing in correspondence to the types of the through-holes.

2. Creation of Masking Data Responsive to Types of Through-Holes

This embodiment is so structured that three types of through-hole diameter masking data are created responsively to the types of the through-holes.

Namely, first masking data are through-hole diameter masking data having identical diameter as compared with measured through-hole diameters, second masking data are through-hole diameter masking data obtained by adding required size (land residual width) to the peripheries of measured through-hole diameters and third masking data are through-hole diameter masking data of prescribed diameters larger than the measured through-hole diameters.

The first masking data are obtained by directly outputting the measured through-hole diameter data i inputted from the second delay circuit 18 in the masking data creating circuit 19. Such processing is directed to obtain a through-hole masking images identical in size to measured images.

The second masking data are created in the following manner: Addition data (converted into pixel numbers) to be added to the peripheries of measured through-hole diameters are previously stored in the masking data memory 20. Then the measured through-hole diameter data inputted from the second delay circuit 18 and the addition data read from the masking data memory 20 are sequentially added in the masking data creating circuit 19. Such processing is directed to create through-hole masking images obtained by adding prescribed width (land residual width) to the peripheral parts of measured images.

The third masking data are created as follows: Through-hole diameter masking data corresponding to masking through-holes slightly larger in diameter than standard through-holes are previously stored in the masking data memory 20. In place of measured through-hole diameter data inputted from the second delay circuit 18, through-hole diameter masking data read from the masking data memory 20 are sequentially outputted in the masking data creating circuit 19. Such processing is directed to create circular through-hole masking images slightly larger than measured images.

selection of these masking functions is performed on the basis of the masking function data $\alpha$ read from the masking data memory 20, as hereinafter described in detail. The masking functions are determined in response to the types of the through-holes in this embodiment.

When no masking processing is required, the masking data creating circuit 19 outputs a signal of "0" on the basis of the masking function data $\alpha$ supplied by the masking data memory 20.

3. Masking Processing of Leading and Trailing Edge Intervals of One Scanning Line The above description has been made on general case in which through-hole images are inputted in circular patterns. In actual masking processing, however, inputted through-holes images may be partially voided in both edge positions of one main scanning line as shown in FIG. 4. In such case, the voided through-hole image must be compared with area values corresponding to the voided portions in area judging processing. Also in diameter judging processing and through-hole diameter masking data creating processing, reading of data must be started from appropriate addresses of the memories 16 and 20 in consideration of the voided positions to perform the respective processing.

In this embodiment, therefore, leading and trailing edge processing intervals of 128 pixels are provided on both ends of one main scanning interval (2592 elements) of the CCD line sensor 3 while an intermediate interval is adapted to perform normal processing as shown in FIG. 4, and prejudge addresses as shown in FIG. 4 are mapped with respective pixel positions. In other words, addresses from "127" to "0" are mapped along the main scanning direction in the leading edge processing interval and addresses of "0" are mapped in the normal processing interval while addresses of "255" to "128" are mapped in the trailing edge processing interval. The pixel numbers in the leading and trailing edge processing intervals can be varied appropriately with the size of the through-holes. Prejudge addresses of the respective through-hole images are determined by addresses corresponding to terminating end positions of the through-hole images in the leading edge processing and normal processing intervals, while those in the trailing edge processing interval are determined by addresses corresponding to front end positions of the through-hole images. Upon such determination of the prejudge addresses, area value data (maximum allowable area data and minimum allowable area data) corresponding to the respective prejudge addresses are set in response to the types of the through-holes. Therefore, these area data are previously calculated by a calculator or the like, to be stored in the prejudge memory 16 while being mapped with the respective prejudge addresses.

The prejudge addresses are created in the timing controller 10 as shown in FIG. 3, to be supplied to the prejudge memory 9. The prejudge memory 9 reads area data corresponding to the supplied prejudge addresses in the area judging circuit 8, which in turn compares the same with calculated through-hole area values. The through-holes are sorted by such comparison, so that type address data responsive to the results of comparison are supplied to the prejudge memory 9 through the selector 12.

On the other hand, the prejudge memory 9 previously stores jumped address data mapped with the type addresses and the prejudge addresses. The jumped address data are adapted to designate reading starting addresses of the pattern data memory 16 and the masking data memory 20, and hence the respective jumped address data are so set that reading of through-hole diameter data and masking processing data from the memories 16 and 20 is started from appropriate addresses responsive to the types and voids of the through-hole images. When the type address data e are supplied to the prejudge memory 9 by the sorting, jumped address data related by the type addresses and the previously supplied prejudge addresses are read from the prejudge memory 9 to be written in the FIFO 13 with the aforementioned structure.

In subsequent diameter judging processing and masking data creating processing, therefore, the through-hole diameter data and the masking processing data are read in order of addresses from the memories 16 and 20, with addresses specified by the aforementioned jumped address data as head addresses, whereby the aforementioned respective processing is appropriately executed in response to the types and voids of the through-hole images.

C. Definite Embodiment

Description is now made on a definite embodiment of the present invention. FIG. 3 is a block diagram showing the pattern masking apparatus. Since the image data creating circuit 5, the masking processing circuit 7, the encoder 6 and the decoder 24 have been schematically described with reference to the principle of pattern masking, the following description is made in detail on the area judging means K, the diameter judging means L and the masking data creating means M.

1. Area Judging Means K (1) Prejudge Memory 9

Description is now made on the memory content of the prejudge memory 9, as schematically shown in FIG. 5. The prejudge memory 9 stores area value data mapped by a 12th bit D-C flag, 8th to 11th bit micro addresses and 0th to 7th bit prejudge addresses and jumped address data mapped by the 12th bit D-C flag, 8th to 11th bit type addresses and 0th to 7th bit prejudge addresses.

The micro addresses are adapted to store data (maximum and minimum areas per type) for sorting, and occupy zero to $F_{Hex}$. Therefore, the same are capable of processing eight types of through-holes. Area data (minimum and maximum values) on eight types of through-holes are stored in order of addresses in response to the sizes of the through-holes in this embodiment.

The prejudge addresses are adapted to process leading and trailing edges, and occupy zero to $7F_{Hex}$.

The D-C flag designates the area data when the content thereof is "0", while designating the jumped address data when the said content is "1".

The type addresses occupy 7 to $F_{Hex}$, and "8" to "F" correspond to respective ones of the eight types of through-holes while "7" corresponds to a pattern applicable to none.

FIG. 6 partially shows the area data of the prejudge memory 9 in detail. Referring to FIG. 6, symbol $D_{1max}$ represents the pixel number of the maximum allowable diameter of the minimum size through-hole, and symbol $D_{1min}$ represents the pixel number of the minimum allowable diameter of the minimum size through-hole. FIG. 7 partially shows the jumped address data of the prejudge memory 9 in detail. Referring to FIG. 7, symbol $D_n$ represents standard diameter pixel numbers of n-th through-holes (n: integers of 1 to 8).

(2) Timing Address Controller 10

Figure 8:
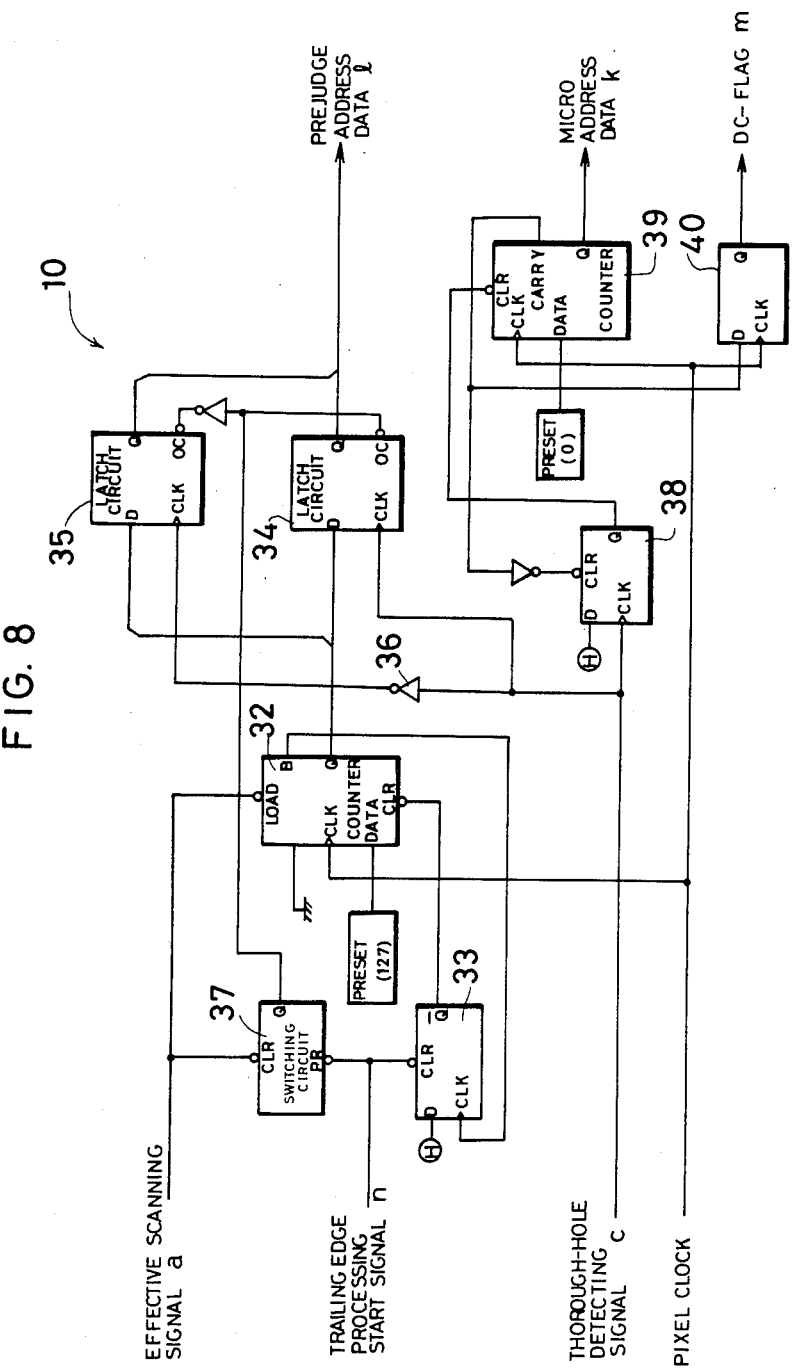
FIG. 8 is a circuit diagram showing a timing address controller in detail.

The timing address controller 10 is adapted to creat micro address data k, prejudge address data l and D-C flag m which are access data for the prejudge memory 9. FIG. 8 is a detailed circuit diagram showing the timing address controller 10, the operation of which is now described.

1. Operation of Prejudge Address Counter

When the scanning position of the CCD line sensor 3 reaches the starting point of the leading edge processing interval as shown in FIG. 4, the effective scanning signal a as shown at FIG. 2(A) rises from "L" to "H". The effective scanning signal a is inputted in a load terminal of a prejudge address counter 32, which is a 256-step down counter, as shown in FIG. 8, whereby the counter 32 is preset at a count value "127". Thereafter the counter 32 is down-counted in accordance with pixel clock signals (i.e., along with progress of main scanning). When the scanning position reaches the starting position of the normal processing interval (FIG. 4), the count value of the counter 32 is turned to "0", whereby the counter 32 outputs a borrow signal to a counter control circuit 33, which in turn supplies an "L" signal from its $\overline{Q}$ terminal to the clear terminal of the counter 32, to stop the operation of the counter 32. The operation-stopped state of the counter 32 continues till a lapse of the normal processing interval as shown in FIG. 4. When the scanning position of the CCD line sensor 3 reaches the starting point of the trailing edge processing interval as shown in FIG. 4, a trailing edge processing start signal n (created in the timing address controller 11, as hereinafter described in detail) is supplied to the clear terminal of the counter control circuit 33 as shown in FIG. 8, whereby an "H" signal is supplied from the $\bar{Q}$ terminal of the control circuit 33 to the clear terminal of the counter 32, which in turn starts its operation again. Thus, the counter 32 is sequentially down-counted from the count value "255". Thus, when the scanning position of the CCD line sensor 3 passes through the trailing edge processing interval as shown in FIG. 4 (the count value of the counter 32 is "128" at this time), the effective scanning signal a as shown at FIG. 2(A) falls from "H" to "L" to be inputted in the load terminal of the counter 32 as an "L" signal, to terminate the counter operation. The aforementioned operation is thus repeated every time main scanning is performed.

2. Creation of Prejudge Address Data l

The count values of the counter 32 are inputted in respective D terminals of a prejudge address latch circuit 34 for the leading edge processing and normal processing intervals and a prejudge address latch circuit 35 for the trailing edge processing interval.

In the clock terminals of the latch circuits 34 and 35, on the other hand, the through-hole detecting signal c (see FIG. 2(C)) is inputted in a direct manner or after inversion by an inverter 36. Therefore, the latch circuit 34 is driven by rising from "L" to "H" of the through-hole detecting signal c corresponding to a hole terminating position of the through-hole image, and the count value at that time is latched as the prejudge address for the leading edge processing or normal processing interval in the latch circuit 34. Further, the latch circuit 35 is driven by fall from "H" to "L" of the through-hole detecting signal c corresponding to a hole beginning position of the through-hole image, and the count value of that time is latched in the latch circuit 35 as the prejudge address for the trailing edge processing interval.

Reading of the prejudge address data latched by the latch circuits 34 and 35 is controlled by a switching circuit 37. In starting of the leading edge processing interval, the switching circuit 37 outputs an "L" signal from its Q terminal by the effective scanning signal a (see FIG. 2(A)) inputted in the clear terminal of the switching circuit 37, whereby the latch circuit 34 is activated. In starting of the trailing edge processing interval, on the other hand, the switching circuit 37 outputs an "H" signal from its Q terminal by the trailing edge processing start signal inputted in the preset terminal of the switching circuit 37, whereby the latch circuit 35 is activated. Thus, prejudge address data l corresponding to the hole terminating positions latched in the latch circuit 34 are read in the leading edge processing and normal processing intervals, while the address data l corresponding to the hole beginning positions latched in the latch circuit 35 are read in the trailing edge processing interval.

3. Creation of Micro Address Data k

When the through-hole detecting signal c (see FIG. 2(C)) rises from "L" to "H" (hole terminating position), the signal c is inputted in the clock terminal of the counter control circuit 38 as shown in FIG. 8, whose Q terminal outputs an "H" signal, which in turn is inputted to a clear terminal of a micro address counter 39 which is a 16-step up counter, whereby a counter clear command is released and the counter operation is started. Namely, after a count value "0" is preset at the counter 39, the same is counted up along clock pulses. The output data from the Q terminal of the counter 39, i.e., count values form the micro address data k.

4. Creation of D-C Flag m

When stepping of the micro address counter 39 is so advanced that its count value exceeds "15", a carry signal is outputted from a carry terminal of the counter 39 to be latched by a D-FF 40. The data latched by the D-FF 40 are read at a subsequent pixel clock, whereby the D-C flag m is created.

(3) Area Judging Circuit 8

Figure 9:
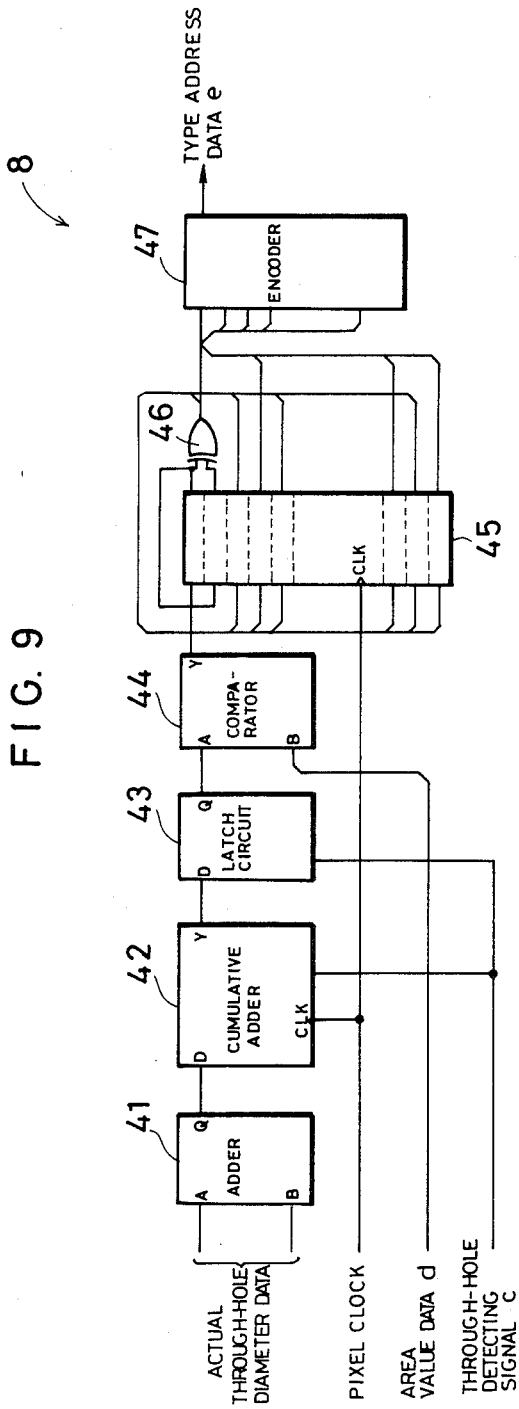
FIG. 9 is a circuit diagram showing an area judging circuit in detail.

The area judging circuit 8 is adapted to calculate area values of through-hole images on the basis of the measured through-hole diameter data b and compares the area valued with area data of the respective through-holes read from the prejudge memory 9, thereby to sort the through-holes. FIG. 9 is a detailed circuit diagram of the area judging circuit 8, the operation of which is now described.

1. Calculation of Area Values

When the measured through-hole diameters are measured by the encoder 6 (FIG. 3), the upper radius data and the lower radius data (measured through-hole diameter data b) thereof are inputted in an adder 41 as shown in FIG. 9, whereby measured through-hole diameters are calculated and the calculated data are transmitted to a cumulative adder 42. The cumulative adder 42 is activated at hole beginning positions (fall from "H" to "L" of the signal c) on the basis of the through-hole detecting signal c (see FIG. 2(C)), to cumulatively add the sequentially transmitted measured through-hole diameter data during intervals of through-hole images (intervals in which the signal c goes low). At the hole terminating positions of the through-hole images, the signal c is switched from "L" to "H", whereby the cumulatively added data, i.e., through-hole area data are latched by a latch circuit 43 in a subsequent stage while the cumulative adder 42 is simultaneously inactivated so that the data in the cumulative adder 42 are cleared.

2. Comparison of Areas

The through-hole area data thus obtained are transmitted to a comparator 44 in a subsequent stage, to be sequentially compared with the through-hole area data d (maximum and minimum allowable areas) of the eight types of through-holes received from the prejudge memory 9.

In this case, the area data of the prejudge memory 9 are read as follows: When the through-hole detecting signal c rises from "L" to "H" to complete the aforementioned area calculation processing, the micro address data k of "0" to "15" are sequentially read from the timing address controller 10 as hereinabove described with reference to FIG. 3, to be supplied to the prejudge memory 9 through the selector 12. During this, the prejudge memory 9 is supplied with data of "0" as the D-C flag m. The data of the D-C flag m is also simultaneously supplied to the selector 12, whereby the selector 12 is switched to supply the micro address data k on the timing address controller 10 side to the prejudge memory 9. Further, the prejudge address data l are supplied to the prejudge memory 9 from the timing address controller 10, as hereinabove described with reference to the timing address controller 10. Thus, area data (see FIGS. 5 and 6) specified by the D-C flag m, the micro addresses k and the prejudge addresses l, i.e., area data (maximum and minimum allowable areas) corresponding to the eight types of through-holes are sequentially read from the prejudge memory 9 to be supplied to the area judging circuit 8.

Thus, the comparator 44 as shown in FIG. 9 sequentially compares the through-hole areas calculated by the cumulative adder 42 and the area data for the respective through-hole images read from the prejudge memory 9. The results of comparison are outputted as, e.g., signals of "1" when the calculated through-hole areas are larger than the area data for comparison and as those of "0" in other case. The compared data thus obtained are transmitted to an uppermost register of a 16-stage shift register 45. The compared data thus transmitted to the uppermost register are shifted to a second register when subsequent compared data are received in the uppermost register. A NOR gate 46 obtains exclusive OR of the compared data in the second register and those of the uppermost register, to shift the result to a third register. Every time compared data are transmitted to the uppermost register thereafter, the NOR gate 46 obtains exclusive OR of the compared data in the uppermost register and the second register to transmit the result to the third register, and thus data in registers following to the third one are sequentially shifted in a downward manner. When all of the data are compared with the maximum and minimum allowable areas with respect to eight types of through-hole, comparison results corresponding to the through-holes types are obtained in even stages of the 16-stage shift register 45. The data of the comparison results are fetched in total to be transmitted to the encoder 47, which in turn encodes the same in response to the through-hole types and outputs the same as the type address data e.

Upon completion of the area comparison processing, the timing address controller 10 as shown in FIG. 3 outputs a signal of "1" as the D-C flag m as hereinabove described with reference to the timing address controller 10, to supply the same to the prejudge memory 9. The data of the D-C flag m are simultaneously supplied to the selector 12, whereby the selector 12 is switched to the area judging circuit 8 side so that the type address data e outputted from the area judging circuit 8 are supplied to the prejudge memory 9 through the selector 12. Thus, jumped address data r (see FIGS. 5 and 7) corresponding to the type address data e prejudge address data l are read from the prejudge memory 9 to be written in the FIFO 13.

(4) Timing Address Controller 11

Figure 10:
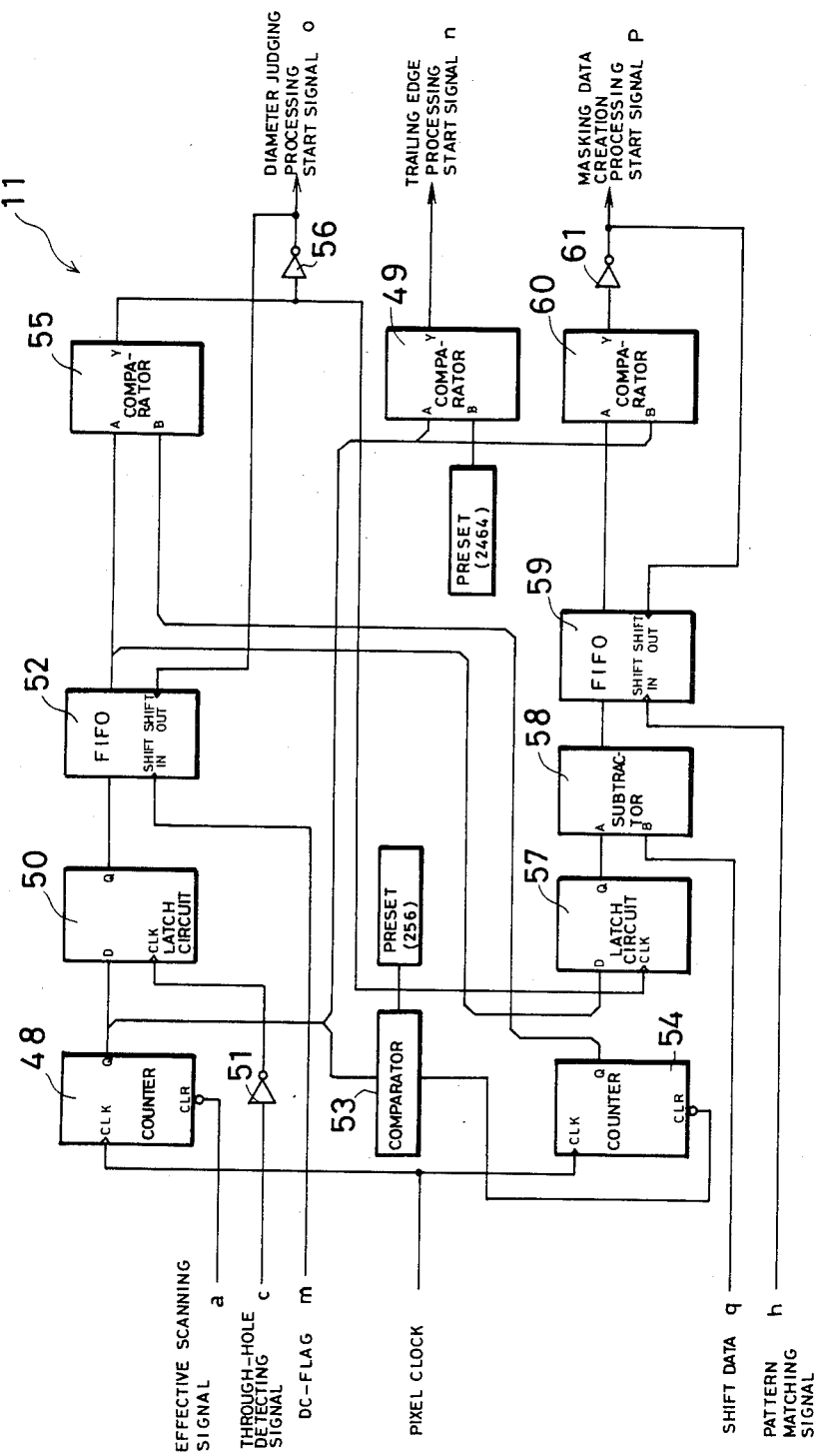
FIG. 10 is a circuit diagram showing the timing address controller in detail.

The timing address controller 11 is adapted to create a trailing edge processing start signal n, a diameter judging processing start signal o and a masking data creation processing start signal p. FIG. 10 is a detailed circuit diagram of the timing address controller 11, the operation of which is now described.

1. Creation of Trailing Edge Processing Start Signal n

When the scanning position of the CCD line sensor 3 reaches the starting point of the leading edge processing interval, the effective scanning signal a as shown at FIG. 2(A) rises from "L" to "H" to be inputted in a clear terminal of an absolute address counter 48 as shown in FIG. 10, which is a 2592-step upper counter, whereby count operation of the counter 48 is started from the count value "0". The count values are sequentially transmitted to an A terminal of a comparator 49. The comparator 49 compares the count values sequentially received in the A terminal with a count value "2464" corresponding to the trailing edge processing start position supplied to its B terminal, to output a trailing edge start signal n when the both count values are matched with each other.

2. Creation of Diameter Judging Processing Start Signal o

The count values of the absolute address counter 48 are also inputted in a latch circuit 50 in addition to the comparator 49. The latch circuit 50 also receives in its clock terminal the through-hole detecting signal c through an inverter 51. Therefore, when the signal c falls from "H" to "L" (hole beginning end position), the current count value of the absolute address counter 48 is latched as absolute address data for the through-hole beginning end position. The absolute address data for the through-hole beginning end position are read in an FIFO 52 when data of "1" are inputted in a shift-in terminal of the FIFO 52 as the D-C flag m, i.e., when the jumped address is determined.

On the other hand, the count values of the absolute address counter 48 are further inputted in another comparator 53. the comparator 53 compares the sequentially received count values with a preset value of "256", so that a clear release command is supplied to a diameter judging processing counter 54 which is a 2592-step up counter when both count values are matched with each other, to start counting operation from a count value "0". In other words, the count operation of the diameter judging processing counter 54 is in a delay by the count value "256" in comparison with the absolute address counter 48. The count values of the counter 54 are inputted in a B terminal of a comparator 55. On the other hand, the comparator 55 receives in its A terminal the output data of the aforementioned FIFO 52, i.e., absolute address data for the through-hole beginning end position. The comparator 55 compares the both data, to output a matching signal "H" when the same are matched with each other. This matching signal "H" is inverted by an inverter 56, whereby the diameter judging processing signal o of the "L" level is created.

The diameter judging processing start signal o is also inputted in a shift-out terminal of the FIFO 52, whereby the said signal o is outputted while subsequent through-hole beginning end position absolute address data are read from the FIFO 52 to be inputted in the comparator 55.

3. Creation of Masking Data Creation Start Signal p

The output signal from a Y terminal of the comparator 55 is also inputted in the clock terminal of the latch circuit 57, and hence the through-hole beginning end position absolute address data of the FIFO 52 are latched in the latch circuit 57 upon generation of the diameter judging processing start signal o (generated when stepping of "256" is made from the absolute address of the through-hole beginning end start position). The through-hole beginning end position absolute address data are transmitted to a subtractor 58 of a subsequent stage, to be subjected to subtraction processing by shift data q received from the pattern data memory 16 (FIG. 3) as hereinafter described in detail. When the pattern matching signal h is outputted from the diameter judging circuit 15 (FIG. 3) as hereinafter described in detail, address data after the aforementioned subtraction processing are transmitted in an FIFO 59 by the signal h.

A comparator 60 positioned in a subsequent stage of the FIFO 59 receives the address data of the FIFO 59 in its A terminal, while receiving count values of the absolute address counter 48 in its B terminal. The comparator 60 compares the both data, to output a matching signal "H" when the same are matched with each other. This matching signal "H" is inverted by an inverter 61, to create the masking data creation processing start signal p of an "L" level. The signal p is outputted when the counting is stepped by about one scanning line from the through-hole beginning end position absolute address value. The signal p is also inputted in the shift-out terminal of the FIFO 59 whereby the said signal p is outputted and subsequent address data are read from the FIFO 59 to be inputted in the comparator 60.

2. Diameter Judging Means (1) Pattern Data Memory 16

Figures 11, 12:
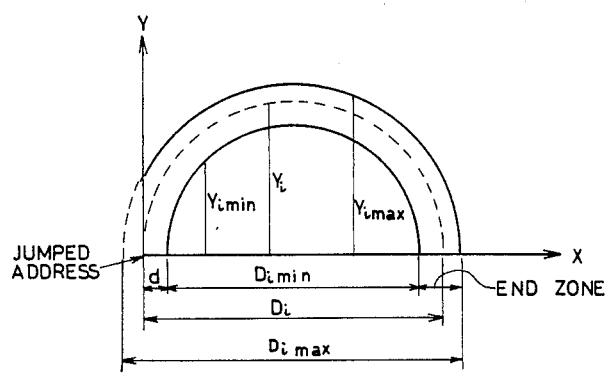
FIG. 11 illustrates data structure of a pattern data memory.
FIG. 12 is a diagram for illustrating the content of the pattern data memory.

Description is now made on the memory content of the pattern data memory 16. This pattern data memory 16 stores data for diameter comparison processing. FIG. 11 shows data structure of the pattern data memory 16.

15th bit end zone data form a flag for determining termination of the diameter comparison processing, and the value thereof is "1" in an end zone as shown in FIG. 11 as hereinafter described in detail, and is "0" in other regions.

14th to 10th bit shift data are those required for timing adjustment in through-hole diameter masking data creation processing in the subsequent stage, as hereinafter described in detail.

9th to 5th bit maximum allowable radius data and 4th to 0th bit minimum allowable radius data are objects of diamter comparison.

FIG. 12 typically shows the memory content of the pattern data memory 16. referring to FIG. 12, a direction X corresponds to the main scanning direction and a direction Y corresponds to the sub-scanning direction. Length along the Y axis direction of a semicircle shown by the dotted line represents a standard through-hole radius $Y_i$ and length along the Y axis direction of an outer semicircle shown by the solid line represents the maximum allowable through-hole radius $Y_{imax}$ while length along the Y axis direction of an inner semicircle shown by the solid line represents the minimum allowable through-hole radius $Y_{imin}$. The through-hole radius $Y_{imax}$ and $Y_{imin}$ arrayed along the X direction (main scanning direction) are stored in the pattern data memory 9 in order of addresses, and the head addresses thereof are mapped with the aforementioned jumped addresses. In FIG. 12, symbol $D_{imin}$ denotes minimum allowable diameter pixel numbers of i-th through-holes (i: integers of 0 to 8), symbol $D_i$ denotes standard diameter pixel numbers of i-th through-holes and symbol $D_{imax}$ denotes maximum allowable diameter pixel numbers. FIG. 13 partially illustrates the detail of data stored in the pattern data memory 16.

(2) Diameter Judging Processing

Figure 14:
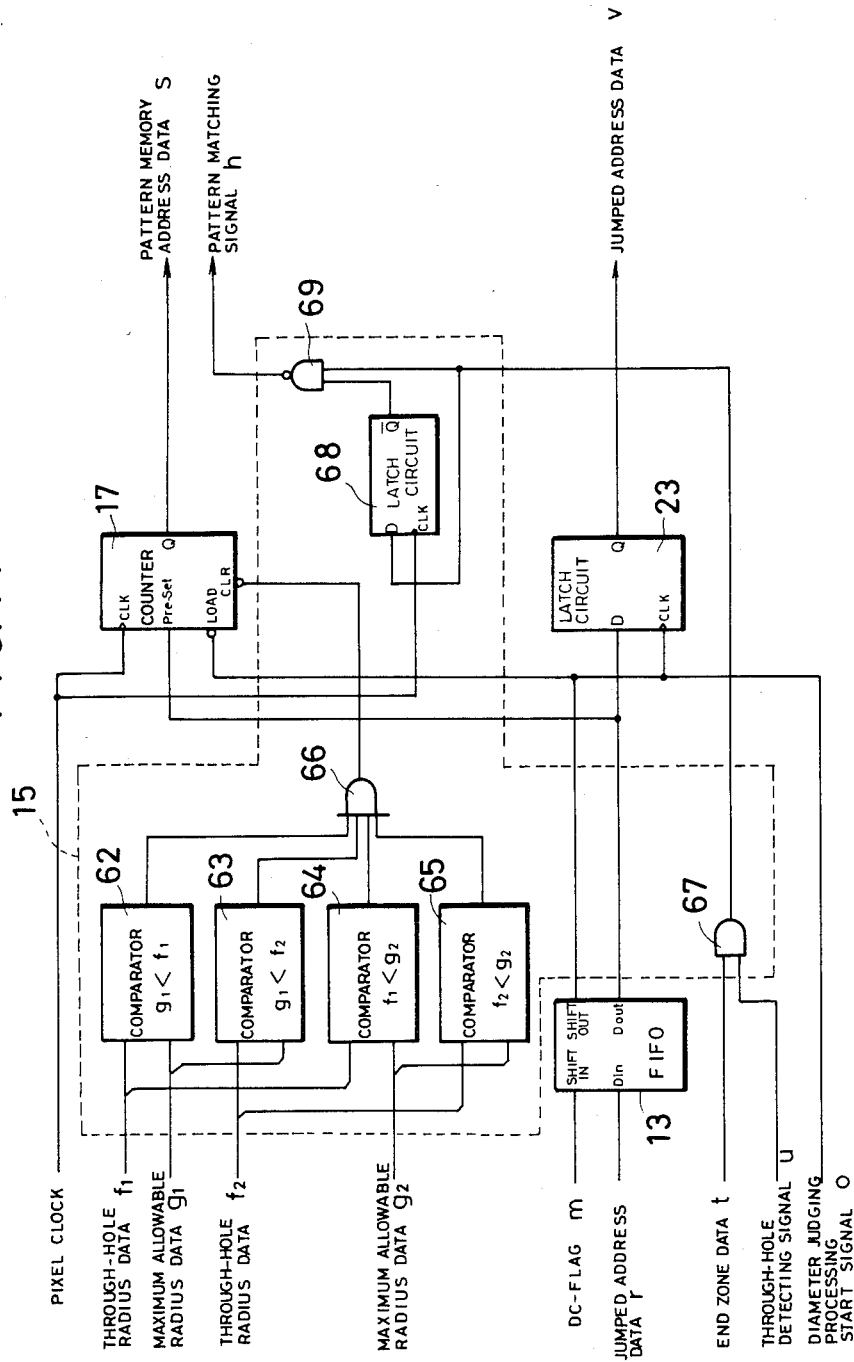
FIG. 14 is a detailed circuit diagram showing an essential part of a diameter judging means.

FIG. 14 is a detailed circuit diagram showing a principal part of the diameter judging means L, i.e., the diameter judging circuit 15 and a part around thereof. Operation for diameter judging processing is now described with reference to FIGS. 14 and 3.

When the measured through-hole diameter data f of a through-hole image beginning end position are inputted from the first delay circuit 14 as shown in FIG. 3 in the diameter judging circuit 15, the measured through-hole diameter data f are separated into upper radius data $f_1$ and lower radius data $f_2$ as shown in FIG. 14, to be inputted in one-side input terminals of comparators 62, 63 and 64, 65 respectively.

In association with the above timing, the diameter judging processing start signal o is inputted from the timing address controller 11 (FIG. 3) in the shift-out terminal (read terminal) of the FIFO 13, whereby the jumped address data latched in the FIFO 13 are latched by the latch circuit 23. Simultaneously with this, the diameter judging processing start signal o is also inputted in the load terminal of the counter 17. Thus, the jumped address data latched in the FIFO 13 are preset in the counter 17, whereby the preset data S (jumped address data) are supplied to the pattern data memory 16 (FIG. 3) so that diameter judging data g mapped with the jumped addresses are read from the pattern data memory 16. The diameter judging data g (minimum allowable radius data $g_1$ and maximum allowable radius data $g_2$) are inputted in other input terminals of the comparators 62, 63 and 64, 65 as shown in FIG. 14 respectively.

The comparator 62 compares each through-hole upper radius $f_1$ with each minimum allowable radius $g_1$ to output an effectuation signal "H" when the through-hole upper radius $f_1$ is larger than the minimum allowable radius $g_1$. The comparator 63 compares each through-hole lower radius $f_2$ with the minimum allowable radius $g_1$, to output an effectuation signal "H" when the through-hole lower radius $f_2$ is larger than the minimum allowable radius $g_1$. Similarly, the comparator 64 compares each through-hole upper radius $f_1$ with the maximum allowable radius $g_2$, to output an effectuation signal "H" when the through-hole upper radius $f_1$ is smaller than the maximum allowable radius $g_2$. The comparator 65 comapares each through-hole lower radius $f_2$ with the maximum allowable radius $g_2$, to output an effectuation signal "H" when the through-hole lower radius $f_2$ is smaller than the maximum allowable radius $g_2$.

The output signals from the respective comparators 62 to 65 are transmitted to an AND gate 66 of a subsequent stage, so that an "H" signal (counter clear release command signal) is supplied to the clear terminal of the up counter 17 when all of the comparators 62 to 65 output the effectuation signals "H", while an "L" signal (counter clear command signal) is supplied when at least one of the comparators 62 to 65 outputs a non-effectuation signal ("L" signal).

Therefore, when all of the results of comparison in the comparators 62 to 65 are effectuated, i.e., the actual through-hole diameters are within the allowable range, the counter 17 is counted up by "1" at a subsequent pixel clock, whereby the diameter judging data g mapped with a subsequent adress of a jumped address are inputted in other input terminals of the comparators 62 to 65 respectively. At this time, subsequent measured through-hole diameter data f are inputted in the one-side input terminals of the comaparators 62 to 65, so that comparison judging processinig is performed in the comparators 62 to 65 similarly to the above through use of these data.

Thus, so far as all of the results of comparison in the comparators 62 to 65 are effectuated, stepping of the counter 17 is continues so that new diameter comparison data g are sequentially transmitted from the pattern data memory 16 to the comparators 62 to 65, which in turn compare the diameter comparison data g with the sequentially received measured through-hole diameter data.

When the measured through-hole diameters are within the allowable range and the diameter comparison processing is advanced to the end zone as shown in FIG. 12, the 15th bit end zone data (see FIGS. 11 and 13) read from the pattern data memory 9 are switched from "0" to "1", so that an "H" signal is supplied to one input terminal of an AND gate 67 as shown in FIG. 14 as end zone data t. When a through-hole image reaches a terminating end position within the range of this end zone (the through-hole image corresponds to the through-hole to be masked in this case), a through-hole detecting signal u (obtained by delaying the through-hole detecting signal c by 256 pixels by the first delay circuit 14) supplied to the other input terminal of the AND gate 67 rises from "L" to "H". Thus, the AND gate 67 outputs an "H" signal, which is inputted in one input terminal of an NAND gate 69 and latched by a latch circuit 68. Simultaneously on the basis of preceding data "L" latched in the latch circuit 68, and "H" signal is supplied from a $\overline{Q}$ terminal of the latch circuit 68 to the other input terminal of the NAND gate 69, whereby the output signal of the NAND gate 69 is switched form "H" to "L". At a subsequent pixel clock, an "L" signal is supplied from the $\overline{Q}$ terminal to the NAND gate 69 on the basis of the data of "H" latched in the latch circuit 68, whereby the output signal of the NAND gate 69 again returns to "H". Thus, when all of the measured through-hole diameters are within the allowable range, the pattern matching signal h of one pulse width is outputted from the diameter judging circuit 15 upon completion of all diameter comparison processing with respect to the through-hole images.

On the other hand, when the results of comparison in th comparators 62 to 65 are at least partially invalidated during the diameter comparison processing (non-through-hole image or defective through-hole in this case), an "L" signal (counter clear command signal) is outputted from the AND gate 66 so that the count value of the counter 17 is cleared at "zero". Thus, data mapped with an address "0", i.e., the data of "0" as shown in FIG. 13 is read as the diameter comparison data from the pattern data memory 16 in the comparators 62 to 65 at a subsequent pixel clock, whereby the results of comparison by the comparators 62 to 65 are continuously invalidated. Thus, the counter 17 is held in a cleared state till all of the diameter comparison processing with respect to the through-hole images is completed. Therefore, the end zone signal is held at "0" (refer to diameter comparison data mapped with address "0" in FIG. 13) during this, so that no pattern matching signal h is outputted from the diameter judging circuit 15.

3. Masking Data Creating Means M
(1) Masking Data Memory 20

Description is now made on the memory content of the masking data memory 20, which stores data required for creating masking data. FIG. 15 shows data structure of the masking data memory 20.

A 7th bit masking termination flag $\beta$ is adapted to indicate termination of the masking processing, and mapped with data of "1" in masking processing intervals while being mapped with data of "0" in non-masking processing intervals.

6th and 5th bit masking function data $\alpha$ are adapted to supply a non-masking processing command and three types of masking processing commands. Table 1 shows relation between the masking function data $\alpha$ and masking functions

TABLE 1

| Processing | Masking Function Data 6H | Masking Function Data 5H | Masking Function |
|---|---|---|---|
| I | 1 | 1 | Inverted Masking Command |
| II | 1 | 0 | Prescribed Diameter Masking Command |
| III | 0 | 1 | Land Residual Width Addition Masking Command |
| IV | 0 | 0 | Non-Masking Processing Command |

In conceptual description of the aforementioned masking functions, the inverted masking command of the processing I is adapted to create through-hole masking images identically sized to the measured images. The prescribed diameter masking command of the processing II is directed to create circular through-hole masking images slightly larger than the measured images. The land residual width addition masking command of the processing III is directed to create through-hole masking images by adding prescribed width (land residual width) to the peripheral parts of the measured images. The non-masking processing command of the processing IV is directed to create no through-hole masking image.

The data contents of the 4th to 0th bit masking data $\theta$ as shown in FIG. 15 are varied with the masking functions (processing I-IV). Table 2 shows relation between the respective processing I-IV and the data contents.

TABLE 2

| Processing | Data Content |
|---|---|
| I | Any Value |
| II | Values of Circular Masking Images of Appropriate Size Regardless of Measured Images |
| III | Values to be Added to Peripheries of Measured Images as Land Residual Width |
| IV | Any Value |

FIG. 16 typically illustrates the memory content of the masking data $\theta$ corresponding to the processing II (prescribed diameter masking command). In FIG. 16, directions X and Y correspond to the main and sub-scanning directions respectively.

Symbol $Y_i$ corresponds to the radius sizes (sizes converted into pixel numbers) of circular images having diameters obtained by adding the land residual width to the maximum allowable diameters on the Y axis direction. These masking data $Y_i$ arrayed along the X direction (main scanning direction) are stored in order of addresses in the masking data memory 20 as the masking data $\theta$, the head addresses of which are mapped with the jumped addresses responsive to the aforementioned types of through-holes.

FIG. 17 typically shows the memory content of the masking data $\theta$ corresponding to the processing III (land residual width addition masking command). The X and Y axes are defined similarly to the case of FIG. 16. Referring to FIG. 17(a), symbol $Y_i$ denotes the masking data. On assumption of a semicircular image B of a standard through-hole as shown at FIG. 17(b) and a semicircular image C having a diameter obtained by adding the land residual width to that of the image B, the masking data $Y_i$ correspond to a value (converted into pixel number) obtained by subtracting the size value of the semicircular image B on the Y axis direction from the size value of the semicircular image C on the Y axis direction. The masking data $Y_i$ arrayed along the X direction (main scanning direction) are stored in address order in the masking data memory 20 as the masking data $\theta$, the head addresses of which are mapped with the jumped addresses responsive to the aforementioned types of the through-holes.

FIG. 18 partially shows the detail of the data stored in the masking data memory 20. As obvious from FIG. 18, the head addresses of the respective processing I to IV are identical to the jumped addresses of the pattern data memory 16. In other words, the masking functions, i.e., the masking processing (I to III) are previously determined in response to the through-hole types. With respect to the 7th bit masking termination flag $\beta$, "1" is stored in all of the addresses in the case of the processing I, while data of "1" are stored in addresses storing the masking data values (not "0") and data of "0" are stored in other addresses in the case of processing II and III.

(2) Masking Data Creation Processing

Figure 19:
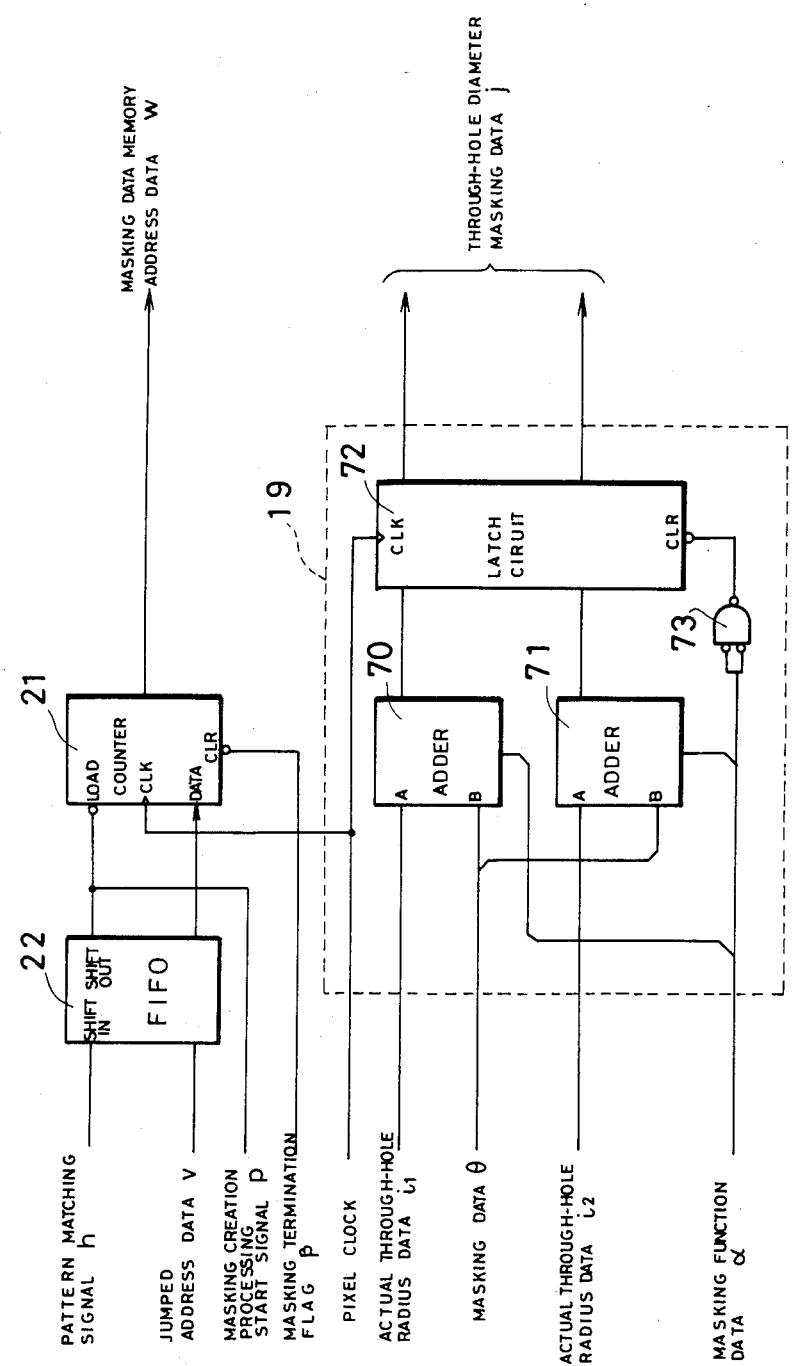
FIG. 19 is a detailed circuit diagram showing an essential part of a masking data creating means.

FIG. 19 is a detailed circuit diagram showing a principal part of the masking data creating means M, i.e., the masking data creating circuit 19 and a peripheral part thereof. The operation for the masking data creation processing is now described with reference to FIGS. 19 and 3. The following description is made on each case, since the operation is varied with the masking functions.

1. In Case of Processing I (Inverted Masking Command)

The jumped address data latched in the latch circuit 23 (FIG. 3) are read in the FIFO 22 when the pattern matching signal h is outputted from the diameter judging circuit 15 (FIG. 3), by input of the signal h in the shift-in terminal (write terminal) of the FIFO 22.

Thereafter when the measured through-hole diameter data i at a through-hole image beginning end position are inputted in the masking data creating circuit 19 by the second delay circuit 18 as shown in FIG. 3, the measured through-hole diameter data i are separated into upper radius data $i_1$ and lower data $i_2$ as shown in FIG. 19, to be inputted in A terminals of adders 70 and 71 respectively.

In association with the said timing, a masking data creation processing start signal p is inputted from the timing address controller 11 (FIG. 3) to the shift-out terminal (read terminal) of the FIFO 22 as well as to the load terminal of the up counter 21. Thus, the jumped address data latched in the FIFO 22 are preset at the counter 21, so that the preset data w (jumped address data) are supplied to the masking data memory 20 (FIG. 3) whereby the masking processing data $\alpha$, $\beta$ and $\theta$ mapped with the jumped address data are read from the masking data memory 20.

Since the case of the processing I (inverted masking command) is assumed here, the data of "1" and "1" (refer to Table 1 and FIG. 18) are inputted in function selecting terminals of the adders 70 and 71 as shown in FIG. 19 as the masking function data $\alpha$. The adders 70 and 71 are adapted to output only input signals of the A terminals when the data of "1" and "1" are inputted in the function selecting terminals thereof, and hence the measured through-hole diameter data $i_1$ and $i_2$ are directly transmitted to a latch circuit 72 of a subsequent stage. On the other hand, the masking function data $\alpha$ are also transmitted to a clear terminal of the latch circuit 72 through a circuit 73. Since "1" and "1" are currently supplied as the masking function data $\alpha$, a "H" signal (clear release signal) is inputted in the clear terminal of the latch circuit 72. Therefore, the measured through-hole diameter data i received in the latch circuit 72 are directly transmitted to the decoder 24 (FIG. 3) of the subsequent stage at a subsequent clock pulse.

While the 6th and 5th bit masking function data $\alpha$ are inputted in the masking data creating circuit 19 as hereinabove described, a 7th bit masking termination flag $\beta$ is simultaneously inputted in the clear terminal of the counter 21. Since "1" (refer to the section of Processing I in FIG. 18) is supplied as the masking termination flag $\beta$, the counter 21 is counted up by "1" at a subsequent pixel clock.

Data on a subsequent address of a jumped address are read from the pattern masking memory 20 by such counting-up, and since the data are identical to the preceding data (refer to the section of Processing I in FIG. 18), masking data creation processing similar to the preceding one is performed. Namely, the measured through-hole diameter data i are directly outputted to the decoder 24 as through-hole diameter masking data j. Thereafter in a similar manner, every time the measured through-hole diameter data i are inputted in the masking data creating circuit 19, through-hole diameter masking data of the same size are sequentially created to be outputted to the decoder 24. Thus, through-hole masking images identically sized to the measured images are created.

2. In Case of Processing II (Prescribed Diameter Masking Command)

The processing II is different from the processing I in that the 6th and 5th bit masking function data $\alpha$ are not "1" and "1", but "1" and "0" (see the section of Processing II in FIG. 18). When "1" and "0" are inputted as the masking function data $\alpha$ in the function selecting terminals of the adders 70 and 71 as shown in FIG. 19, the adders 70 and 71 are so switched as to output signals received in the B terminals in place of those received in the A terminals to the latch circuit 72. Since the 4th to 0th bit masking data $\theta$ stored in the masking data memory 20 are inputted in the B terminals of the adders 70 and 71, the through-hole masking images created by the masking data creating circuit 19 are circular images specified by the masking data $\theta$ sequentially read from the masking data memory 20, i.e., circular images of prescribed diameters slightly larger in diameter than the measured through-hole images.

For matching in timing with the measured images, it is necessary to read the data from the masking data memory 20 faster by the land residual width than in the case of the processing I. Therefore, data corresponding to the land residual width are stored as shift data in corresponding areas of the pattern data memory 16 (see 14th to 10th bit data $L_n$ in FIG. 13) in this embodiment, to transmit the corresponding shift data $L_n$ to the address controller 11 in the diameter comparison processing, thereby to generate the masking data creating signal p at timing faster by the land residual width than the case of the processing I (as to the detail, refer to the above description on the address controller 11). Other operation is similar to that of the processing I.

3. In Case of Processing III (Land Residual Width Addition Masking Command)

The processing III is different from the processing II in that 6th and 5th masking function data $\alpha$ are "0" and "1" in place of "1" and "0" (refer to the section of Processing III in FIG. 18). When "0" and "1" are inputted in the function selecting terminals of the adders 70 and 71 as shown in FIG. 19 as the masking function data α, the adders 70 and 71 are switched to add up the measured through-hole diameter data $i_1$ and $i_2$ received in the A terminals with the masking data θ read from the masking pattern memory 20, to output the added data to the latch circuit 72. The masking data θ sequentially read from the masking pattern memory 20 are those to be added as the land residual width, and hence the masking data creating circuit 19 creates through-hole masking images obtained by adding the land residual width to the peripheral parts of the actual images. Other operation is similar to that of the processing II.

4. In Case of Processing IV (Non-Masking Processing Command)

When no pattern matching signal h is outputted from the diameter judging circuit 15 (FIG. 3), the count value of the counter 21 is "0" and the masking data memory 20 supplies data of "0" and "0" to the masking data creating circuit 19 as the masking function data α (refer to the section of Processing IV in FIG. 18). The masking function data α Of "0" and "0" are supplied to the AND gate 73 as shown in FIG. 19 so that a data clear command ("L" signal) is inputted in the clear terminal of the latch circuit 72, which in turn outputs data of "0". In other words, no through-hole masking image is created in the case of the processing IV.

Description on the masking processing performed after creation of the masking data is omitted, since the same has already been described with reference to the masking principle.

D. Effect of First Embodiment

According to the first embodiment as hereinabove described, the through-hole patterns can be automatically detected for masking, thereby to enable defect inspection of objects having through-holes by the pattern matching method. The area judging circuit 8 sorts the through-holes, whereby masking processing can be performed on a plurality of types of through-holes. Further, the masking data creating circuit 19 can perform three types of masking processing in response to the through-hole types on the basis of the masking processing data received from the masking data memory 20. In addition, the leading and trailing edge processing intervals mapped by prejudge addresses are provided to determine jumped addresses of the memories 16 and 20, whereby masking processing can also be performed on images whose through-holes are voided in the said intervals.

(II) Second Embodiment

Description is now made on a second embodiment of the present invention.

A. Structure of Essential Part of Pattern Masking Apparatus

Figure 20B:
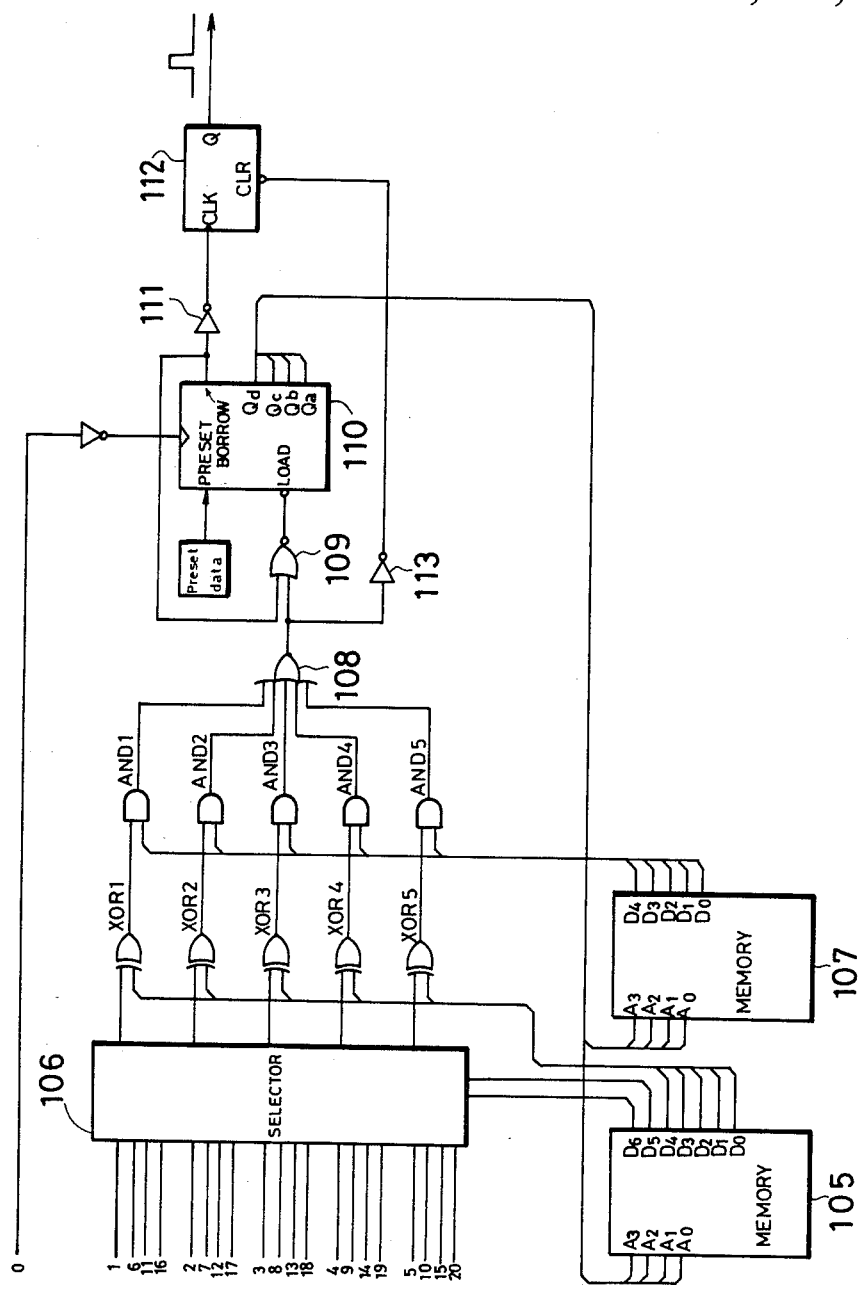
FIG. 20, consisting of FIGS. 20A and 20B, is a circuit diagram showing an essential part of a pattern masking apparatus according to a second embodiment of the present invention.

FIG. 20 is a circuit diagram showing an essential part of a pattern masking apparatus according to the second embodiment of the present invention. This circuit has such a function of inputting image data of inspected objects to determine whether or not the patterns of the inputted images correspond to a standard through-hole pattern. It is assumed here, for convenience of illustration, that through-hole patterns to be determined are smaller than 5×5 pixels in size, although any size of patterns can be theoretically determined.

An inspected pattern corresponding to an inspected object 101 is inputted by an input device 102 such as a line sensor, area sensor or TV camera, so that the image data thereof are binarized by a subsequent binarizing circuit 103. For convenience of illustration, it is assumed here that the input device 102 is a CCD line sensor of 2048 pixels so that the inspected object 101 is moved by one pixel in the sub-scanning direction y every time the CCD line sensor performs scanning by one line in the main scanning direction X, thereby to obtain image data over the entire surface of the inspected object 101.

The image data binarized by the binarizing circuit 103 are sequentially latched by a flip-flop $P_1$ in response to pixel clock pulses generated from a pixel clock generator 104. On the other hand, image data delayed by one scanning line (2048 pixels) through a 2043-bit line shift register $L_1$ and flip-flops $P_6$ to $P_{10}$ for five pixels are latched by a flip-flop $P_2$. Thereafter in a similar manner, image data delayed by two scanning intervals through a 2043-bit line shift register $L_2$ and flip-flops $P_{11}$ to $P_{15}$ for five pixels are latched by a flip-flop $P_3$, image data delayed by three scanning intervals through a 2043-bit line shift register $L_3$ and flip-flops $P_{16}$ to $P_{20}$ are latched by a flip-flop $P_4$ and image data delayed by four scanning intervals through a 2048-bit line shift register $L_4$ are latched by a flip-flop $P_5$. Thus, image data for five pixels in the same array in the sub-scanning direction sequentially appear at the flip-flops $P_1$ to $P_5$ per pixel clock pulse. Further, image data one to five pixels ahead of those latched by the flip-flop $P_2$ along the time-series direction (main scanning direction) appear at the flip-flops $P_6$ to $P_{10}$. Similarly, image data one to five pixels ahead of those latched in the flip-flop $P_3$ along the time-series direction appear at the flip-flops $P_{11}$ to $P_{15}$ and image data one to five pixels ahead of those latched by the flip-flop $P_4$ along the time-series direction appear at the flip-flops $P_{16}$ to $P_{20}$.

In this case, the line shift registers $L_1$ to $L_5$ and the flip-flops $P_1$ to $P_{20}$ form image data creating means.

A memory 105 stores a first standard image data group formed by image data for five pixels in the sub-scanning direction and five pixels in the main scanning direction as those representing a standard through-hole pattern to be recognized, a second standard image data group one to five pixels ahead thereof along the main scanning direction for preceedingly checking pattern matching in the time-series direction and selector switching data. On the basis of address signals received in input terminals $A_3$ to $A_0$, the memory 105 outputs the said selector switching data from output terminals $D_5$ and $D_6$ to a selector 106, while outputting the second or first standard image data group to one-side input terminals of exclusive OR circuits XOR1 to XOR5 from output terminals $D_4$ to $D_0$. These data are outputted on leading edges of pixel clock pulses, as hereinafter described in detail.

On the basis of the selector switching data outputted from the memory 105, the selector 106 makes any five-pixel image data in the flip-flops $P_1$ to $P_5$, $P_6$ to $P_{10}$, $P_{11}$ to $P_{15}$ and $P_{16}$ to $P_{20}$ selectively inputted in other input terminals of the exclusive OR circuits XOR1 to XOR5. Thus, the exclusive OR circuits XOR1 to XOR5 compare image data of corresponding pixels, to output "1" when the same are mismatched with each other.

When no inspection is required in an area within a region (5×5 pixels) to be inspected, a memory 107 stores masking data for masking the results of inspection of the area. On the basis of address signals supplied to input terminals $A_3$ to $A_0$ of the memory 107, the masking data are supplied to oneside input terminals of AND circuits AND1 to AND5. The other input terminals of the AND circuits AND1 to AND5 receive output signals from the exclusive OR circuits XOR1 to XOR5, and when "0" is inputted as making data in any of the AND circuits AND1 to AND5, the said AND circuit outputs "0" even if the corresponding one of the exclusive OR circuits XOR1 to XOR5 outputs "1" (in case of mismatch) as hereinafter described in detail.

Respective output signals from the AND circuits AND1 to AND 5 are inputted in an OR circuit 108, whose output is subjected to NOR with a borrow signal from a counter 110 in a NOR circuit 109, to be inputted in a load terminal of the counter 110. Although the counter 110 may be implemented by either an addition counter or a subtraction counter, it is assumed here that the same is a subtraction counter loaded with "5" as preset data, for convenience of illustration. Further, the counter 110 is assumed to be a synchronized type counter, which executes respective functions on the trailing edges of the pixel clock pulses. Data corresponding to the count values of the counter 110 are inputted in the input terminals of the memories 105 and 107 as address data respectively. The borrow signal from the counter 110 is inverted by an inverter 111 to be inputted in a monostable oscillator 112, which outputs a pattern matching signal on the trailing edges of the borrow signal.

In this case, the memories 105 and 107, the selector 106, the exclusive OR circuits XOR1 to XOR5, the AND circuits AND1 to AND5, the OR circuit 108, the NOR circuit 109, the counter 110 and the monostable oscillator 112 form a pattern judging means.

B. Operation of Pattern Masking Apparatus

Pattern Example 1

Figure 21:
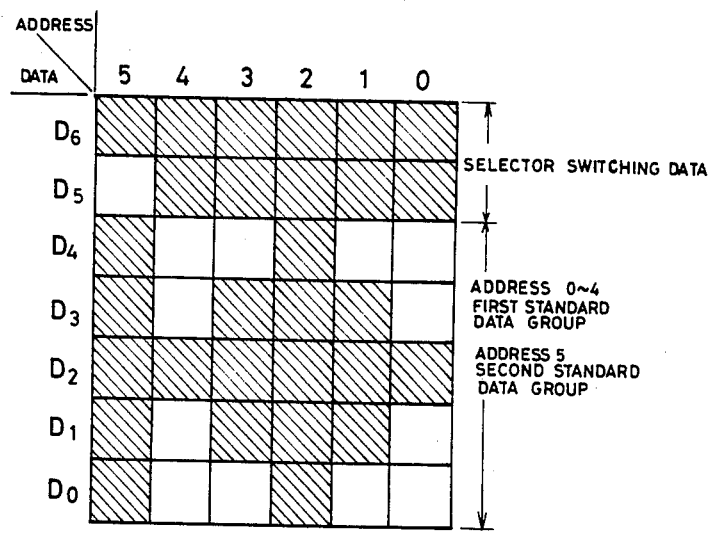
FIG. 21 illustrates memory data stored in a memory.
Figure 24:
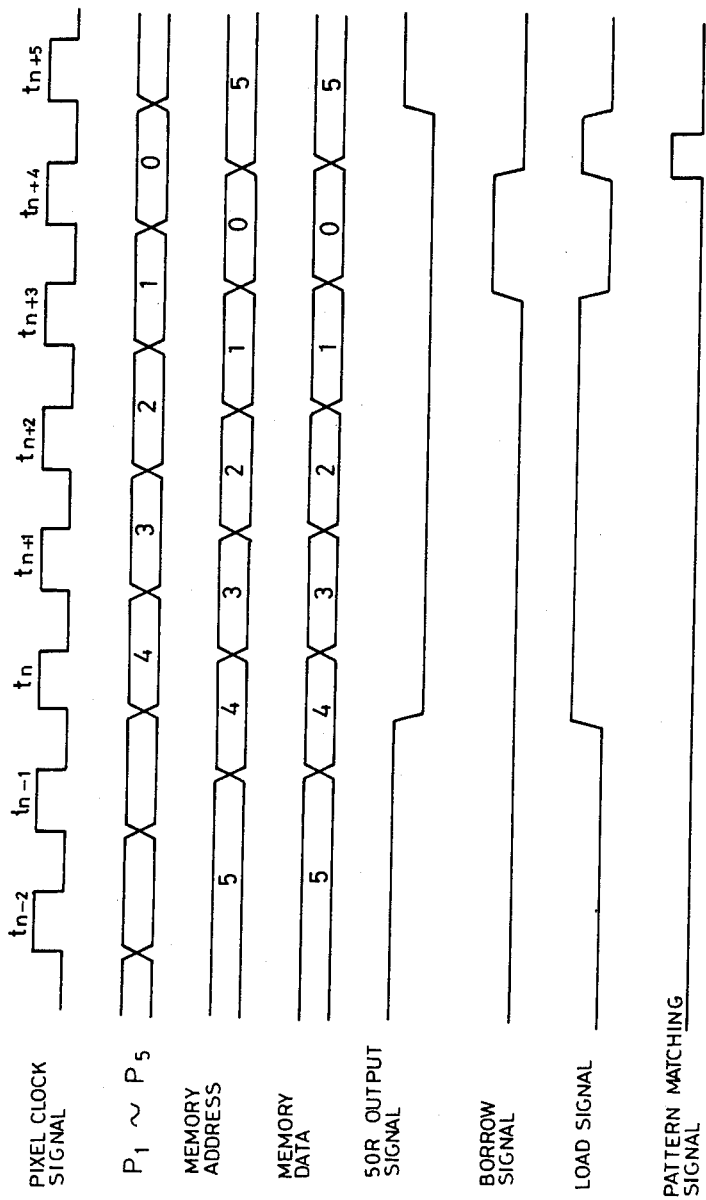
FIG. 24 is a timing chart for illustrating the operation of the pattern masking apparatus.

Description is now made on the operation of the circuit part of the pattern masking apparatus as shown in FIG. 20 with respect to definite pattern example, with reference to a timing chart as shown in FIG. 24. It is assumed here that the memory 104 stores memory data as shown in FIG. 21. In this case, data $D_0$ to $D_4$ corresponding to addresses "0" to "4" represent through-hole pattern data (first standard image data group) to be recognized. Data $D_0$ to $D_4$ corresponding to an address "5" represent a second standard image data group for preceedingly checking pattern matching in the time-series direction. Data $D_5$ and $D_6$ corresponding to addresses "0" to "5" represent selector switching data. The second standard image data group is a group of image data identical to those (data $D_2$ of addresses "0" to "4") in a column in the main scanning direction corresponding to the flip-flops ($P_{11}$ to $P_{15}$) selected by the selector switching data. Referring to FIG. 21, slant regions represent "0" and vacant regions represent "1". The following Table is a truth-value table of the selector 106:

| $D_5$ | $D_6$ | Selector Output |
|---|---|---|
| 0 | 0 | $P_1$ to $P_5$ |
| 0 | 1 | $P_6$ to $P_{10}$ |
| 1 | 0 | $P_{11}$ to $P_{15}$ |
| 1 | 1 | $P_{16}$ to $P_{20}$ |

Figure 22:
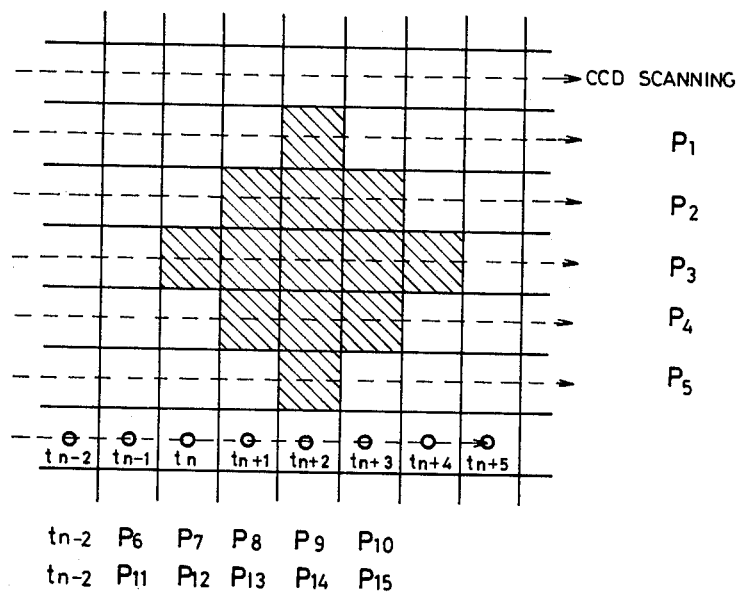
FIG. 22 illustrates a through-hole pattern of an inspected object.

It is assumed here that the inspected object 101 has a through-hole pattern as shown in FIG. 22. Further, it is assumed that the memory 107 is entirely written with "1".

At a time $t_{n-2}$ in FIG. 22, a pattern at FIG. 23(a) is inputted in the flip-flops $P_1$ to $P_5$. A pattern at FIG. 23(g) is inputted in the flip-flops $P_6$ to $P_{10}$ and $P_{16}$ to $P_{20}$ while a pattern at FIG. 23(h) is inputted in the flip-flops $P_{11}$ to $P_{15l}$. Since the counter 110 is preset at "5" by a load signal at this time, data on the address "5" are called from the memory 105, whereby the selector 106 selects the flip-flops $P_{11}$ to $P_{15}$. As the result, the data of FIG. 23(h) latched in the flip-flops $P_{11}$ to $P_{15}$ are inputted in one-side input terminals of the exclusive OR circuits XOR1 or XOR5 while the second standard image data group, i.e., the data ($D_4$ to $D_0$) of the address "5" as shown in FIG. 21 are inputted in other-side input terminals, whereby the exclusive OR circuit XOR1 outputs "1". Thus, the OR circuit 108 also outputs "1", so that the counter 110 is loaded and the counter value is continuously preset at "5" on the trailing edge of the pixel clock pulse.

Then, at a time $t_{n-1}$, the pattern at FIG. 23(a) is inputted in the flip-flops $P_1$ to $P_5$ and the pattern at FIG. 23(i) is inputted in the flip-flops $P_{11}$ to $P_{15}$. Since the counter 110 is preset at "5" at this time as hereinabove described, the selector 106 continuously selects the flip-flops $P_{11}$ to $P_{15}$. Therefore, the exclusive OR circuits XOR1 to XOR5 receive the data at FIG. 23(i) latched in the flip-flops $P_{11}$ to $P_{15}$ and the second standard image data group, i.e., the data ($D_4$ to $D_0$) of the address "5" as shown in FIG. 21. Since these patterns are matched, all of the exclusive OR circuits XOR1 to XOR 5 output "0". As the result, the OR circuit 108 outputs "0" and the counter 110 is loaded at "1". Thus, the counter 110 is subtracted on the trailing edge of the pixel clock pulse, whereby output terminals $Q_a$ to $Q_d$ output the address "4".

Thereafter at a time $t_n$, a subsequent pattern, i.e., that of FIG. 23(b) is latched by the flip-flops $P_1$ to $P_5$ on the leading edge of the pixel clock pulse. Further, data ($D_6$ to $D_0$) of the address "4" as shown in FIG. 21 are called from the memory 105. Since the data $D_6$ and $D_5$ are "0" and "0" in this case, the selector 106 is switched from the flip-flops $P_{11}$ to $P_{15}$ to the flip-flops $P_1$ to $P_5$. Therefore, the exclusive OR circuits XOR1 to XOR5 receive the data of FIG. 23(b) latched in the flip-flops $P_1$ to $P_5$ and the data ($D_4$ to $D_0$) of the address "4" as shown in FIG. 21. Since the patterns are matched also in this case, all of the exclusive OR circuits XOR1 to XOR5 output "0". As the result, the OR circuit 108 outputs "0" and the counter 110 is loaded at "1". Thus, the counter 110 is subtracted on the trailing edge of the pixel clock pulse, whereby the output terminals $Q_a$ to $Q_d$ of the counter 110 output address data "3".

Thereafter in a similar manner, the pattern of FIG. 23(c) is latched in the flip-flops $P_1$ to $P_5$ on the leading edge of the pixel clock pulse at a time $t_{n+1}$ and the data ($D_6$ to $D_0$) of the address "3" as shown in FIG. 21 are called from the memory 105. Thus, the selector 106 continuously selects the flip-flops $P_1$ to $P_5$, and the data of FIG. 23(c) and the data ($D_4$ to $D_0$) of the address "3" as shown in FIG. 21 are inputted in the exclusive OR circuits XOR1 to XOR5, whereby all of the exclusive OR circuits XOR1 to XOR5 output "0". As the result, the OR circuit 108 outputs "0" and the counter 110 is loaded at "1", whereby the counter 110 is subtracted on the trailing edge of the pixel clock pulse to output address data "2" from the output terminals $Q_a$ to $Q_d$ thereof.

On the leading edge of the pixel clock pulse at a subsequent time $t_{n+2}$, the pattern of FIG. 23(d) is latched in the flip-flops $P_1$ to $P_5$ while the data ($D_6$ to $D_0$) of the address "2" as shown in FIG. 21 are called from the memory 105. Thus, the selector 106 continuously selects the flip-flops $P_1$ to $P_5$, and the exclusive OR circuits XOR1 to XOR5 receive the data of FIG. 23(d) and the data ($D_4$ to $D_0$) of the address "2" as shown in FIG. 21, whereby all of the exclusive OR circuits XOR 1 to XOR5 output "0". As the result, the OR circuit 108 outputs "0" and the counter 110 is loaded at "1", whereby the counter 110 is subtracted on the trailing edge of the pixel clock pulse to output address data "1" from the output terminal $Q_a$ to $Q_d$ thereof.

On the leading edge of the pixel clock pulse at a subsequent time $t_{n+3}$, the pattern of FIG. 23(e) is latched by the flip-flops $P_1$ to $P_5$, while the data ($D_6$ to $D_0$) of the address "1" as shown in FIG. 21 are called from the memory 105. Thus, the selector 106 continuously selects the flip-flops $P_1$ to $P_5$, and the exclusive OR circuits XOR1 to XOR5 receive the data of FIG. 23(e) and the data ($D_4$ to $D_0$) of the address "1" as shown in FIG. 21, whereby all of the exclusive OR circuits XOR1 to XOR5 output "0". As the result, the OR circuit 108 outputs "0". While the load signal of the counter 110 is "1" at this time, the counter 110 is subtracted on the trailing edge of a subsequent clock pulse to output "0" as address data and the borrow signal becomes "1", whereby the load signal is switched to "0" by the NOR circuit 109.

On the leading edge of the pixel clock pulse at a subsequent time $t_{n+4}$, the pattern of FIG. 23(f) is latched by the flip-flops $P_1$ to $P_5$, while data ($D_6$ to $D_0$) of the address "0" as shown in FIG. 21 are called from the memory 105. Thus, the selector 106 continuously selects the flip-flops $P_1$ to $P_5$, while the exclusive OR circuits XOR 1 to XOR5 receive the data of FIG. 23(f) and the data ($D_4$ to $D_0$) of the address "0" as shown in FIG. 21, whereby all of the exclusive OR circuits XOR1 to XOR5 output "0". As the result, the OR circuit 108 outputs "0". Since the borrow signal of the counter 110 is "1" at this time, the load signal is continuously held at "0" by the NOR circuit 109. Therefore, "5" is preset at the counter 110 on the trailing edge of the subsequent pixel clock pulse, whereby the output terminals $Q_a$ to $Q_d$ of the counter 110 output the address data "5". The borrow signal is simultaneously switched from "1" to "0". This borrow signal is inverted by the inverter 111 to be inputted in a clock terminal of a monostable oscillator 112. Clearing of the monostable oscillator 112 is released at this time since its clear terminal receives the "1" signal obtained by inversion of the output signal "0" of the OR circuit 108 by the inverter 113. As the result, the monostable oscillator 112 outputs a pattern detecting signal from its output terminal Q.

On the leading edge of the pixel clock pulse at a subsequent time $t_{n+5}$, the flip-flops $P_1$ to $P_5$ latch the pattern of FIG. 23(a) while the flip-flops $P_{11}$ to $P_{15}$ latch the pattern of FIG. 23(j). The data ($D_6$ to $D_0$) of the address "5" are called from the memory 105, whereby the selector 106 is switched from the flip-flops $P_1$ to $P_5$ to the flip-flops $P_{11}$ to $P_{15}$. As the result, the exclusive OR circuits XOR1 to XOR5 receive the data of FIG. 23(j) latched in the flip-flops $P_{11}$ to $P_{15}$ and the data ($D_4$ to $D_0$) of the address "5" as shown in FIG. 21. Since these data are mismatched, the OR circuit 108 outputs "1". As the result, the load signal of the counter 110 is switched from "1" to "0", whereby "5" is preset at the counter 110 on the trailing edge of the pixel clock pulse to output the address data "5" from the output terminals $Q_a$ to $Q_d$ thereof.

Thus, when the image data latched in the flip-flops $P_1$ to $P_5$ in a time-series manner and the first standard image data (5×5 pixels) stored in the memory 105 are entirely matched, i.e., when the pattern of an inputted image is matched with the standard through-hole pattern, the monostable oscillator 112 outputs the pattern matching signal.

Operation Example 2

Figure 25:
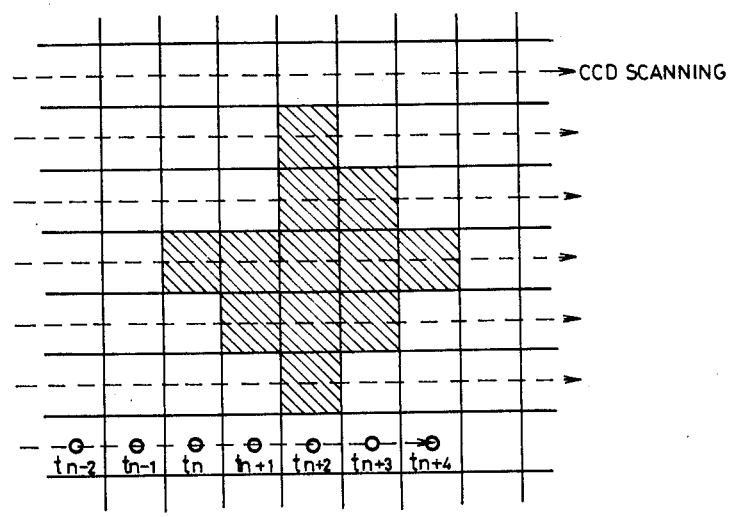
FIG. 25 illustrates a pattern on an inspected surface.
Figures 26A, 26B:
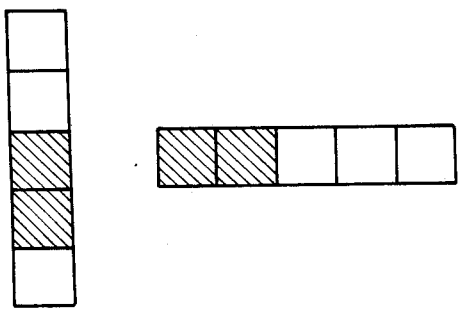
FIG. 26 A and B illustrates data latched in flip-flops.

Description is now made on operation in case where the pattern of an inputted image is mismatched with a standard through-hole pattern (first standard image data) in the aforementioned circuit, with reference to FIG. 25 showing an example of the inputted pattern. During an interval between times $t_{n-2}$ and $t_n$, operation similar to the case of the inputted pattern as shown in FIG. 22 is performed. At a subsequent time $t_{n+1}$, the flip-flops $P_1$ to $P_5$ latch a pattern of FIG. 26(a) and the exclusive OR circuits XOR1 to XOR5 receive the data of FIG. 26(a) and the data ($D_4$ to $D_0$) of the address "3" as shown in FIG. 21. Since these data are partially mismatched, the exclusive OR circuit XOR2 corresponding to the mismatched portion outputs "1". As the result, the OR circuit 108 outputs "1" and the load signal of the counter 110 becomes "0", whereby "5" is preset at the counter 110 on the trailing edge of the pixel clock pulse, to output address data "5" from the output terminals $Q_a$ to $Q_d$ thereof.

Therefore, the selector 106 is switched from the flip-flops $P_1$ to $P_5$ to the flip-flops $P_{11}$ to $P_{15}$ on the leading edge of a pixel clock pulse at a subsequent time $t_{n+2}$. Since the flip-flops $P_{11}$ to $P_{15}$ latch the pattern of FIG. 26(b) at this time, the exclusive OR circuits XOR1 to XOR5 receive the data of FIG. 26(b) and the data ($D_4$ to $D_0$) of the address "5" as shown in FIG. 21. Since these data are also partially mismatched, the OR circuit 108 outputs "1" and the load signal of the counter 110 becomes "0". Therefore, "5" is continuously preset at the counter 110 on the trailing edge of a subsequent pixel clock pulse, so that the address data "5" are outputted from the output terminals $Q_a$ to $Q_d$ of the counter 110.

Thereafter operation similar to the above is performed at times $t_{n+3}$, $T_{n+4}$, ... Thus, if the inputted image pattern is at least partially mismatched with the standard through-hole pattern, the monostable oscillator 112 outputs no pattern matching signal. In this example, the pattern matching signal is outputted when the patterns are matched continuously by six times.

When the monostable oscillator 112 outputs the pattern machine signal, processing for creating through-hole diameter masking data is started on the basis thereof in a similar method to that of the first embodiment, to sequentially perform masking processing on the image data of the inputted image through use of the created through-hole diameter masking data. Thus, the through-hole pattern is masked.

Figure 27:
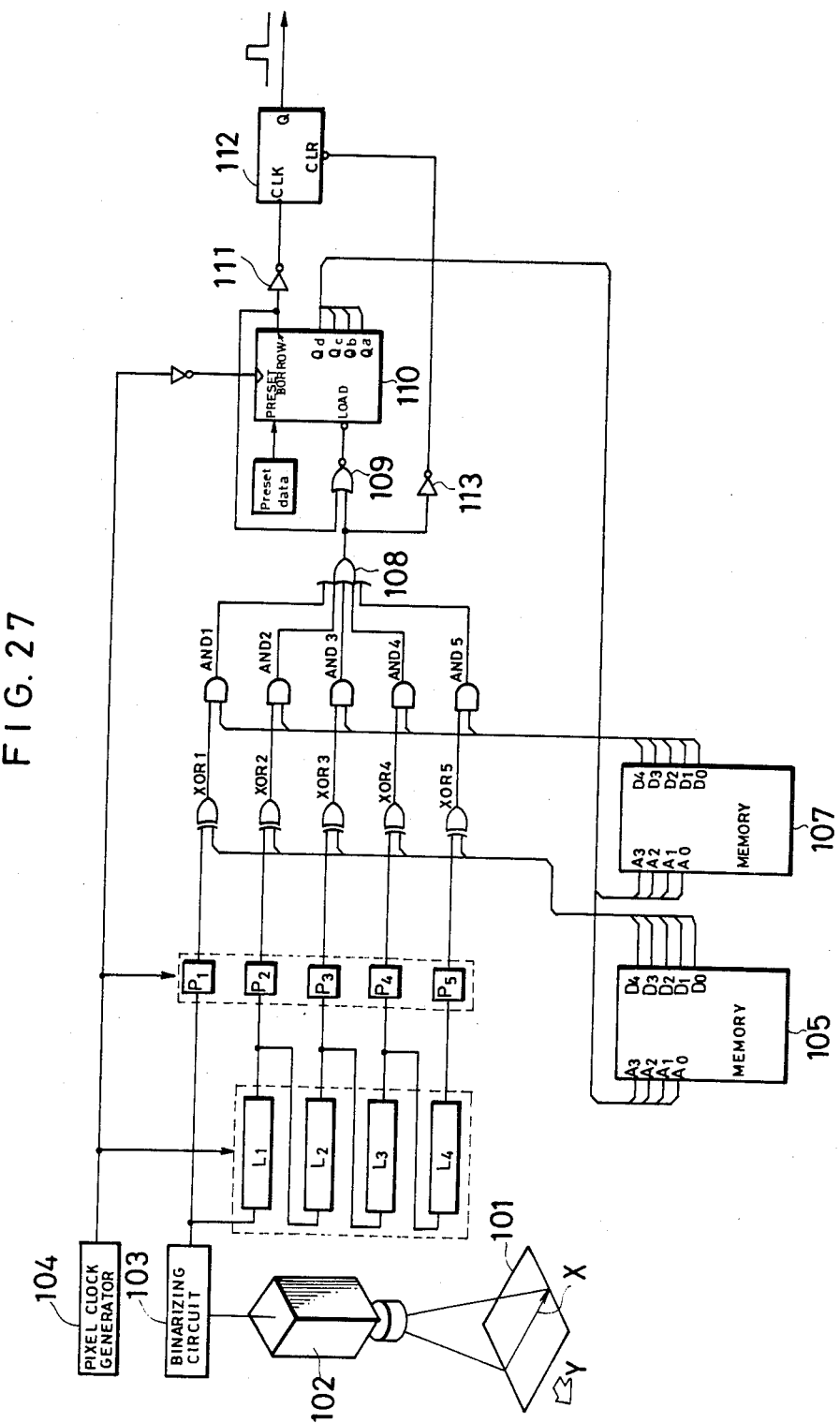
FIG. 27 illustrates a modified circuit of the second embodiment.

The flip-flops $P_6$ to $P_{20}$ for precedingly checking pattern matching in the time series direction and the selector 106 for switching the flip-flops as shown in FIG. 20 may be omitted as shown in FIG. 27. In this case, the line shift registers $L_1$ to $L_3$ are implemented by those of 2048 bits similarly to the line shift register $L_4$. The counter 110 is made to have a preset value of "4". The memory 105 stores only the first standard image data group, i.e., the data ($D_4$ to $D_0$) of the addresses "0" to "4" in FIG. 21.

Operation Example 3, Pattern Example 2

Figure 28:
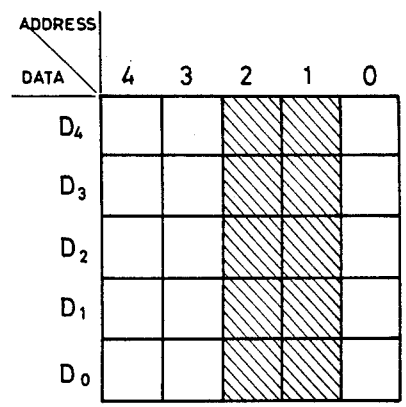
FIG. 28 illustrates memory data stored in a memory.
Figures 30A, 30B:
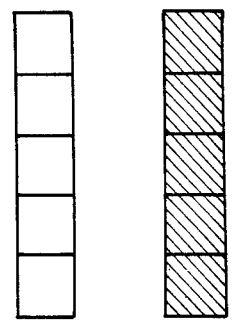
FIG. 30 A and B illustrates data latched in flip-flops.
Figure 29:
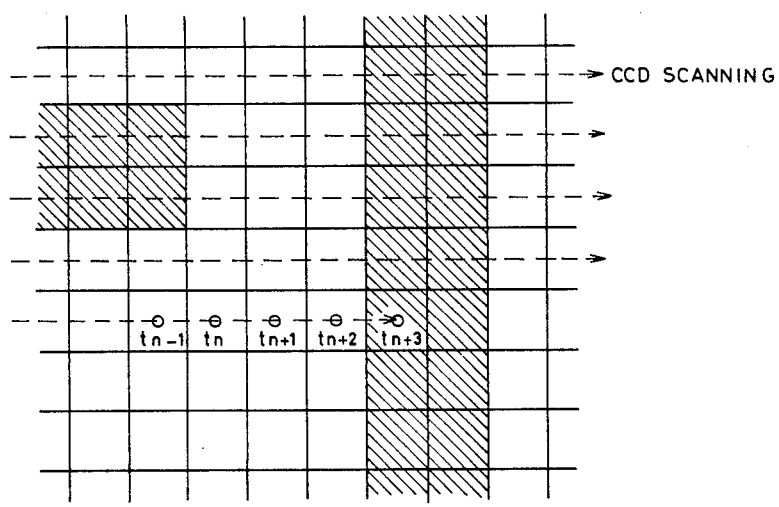
FIG. 29 illustrates a pattern on an inspected surface.

Description is now made on the functions of the flip-flops $P_6$ to $P_{20}$ and the selector 106 for switching the flip-flops as shown in FIG. 20. In a circuit as shown in FIG. 27 provided with no such elements, a recognition error may be caused in recognition of a pattern corresponding to lines or line width as shown in FIG. 28. The reason for this is as follows: It is assumed here that the memory 105 stores the standard pattern data as shown in FIG. 28 and an inspected surface has a pattern as shown in FIG. 29. In this case, the flip-flops $P_1$ to $P_5$ latch data as shown at FIG. 30($a$) at the time $t_n$, to compare the same with data ($D_4$ to $D_0$) of an address "4" as shown in FIG. 28. Since these data are matched with each other, the counter 110 is subtracted to have a count value of "3". At the subsequent time $t_{n+1}$, the flip-flops $P_1$ to $P_5$ similarly latch the data of FIG. 30($a$) to compare the same with data ($D_4$ to $D_0$) of an address "3" as shown in FIG. 28. Since these data are also matched with each other, the counter 110 is subtracted to have a count value of "2". At the subsequent time $t_{n+2}$, however, the flip-flops $P_1$ to $P_5$ also latch the data of FIG. 30($a$), which are mismatched with data ($D_4$ to $D_0$) of an address "2" as shown in FIG. 28. Therefore, the counter 110 is preset at "4" by the said comparison of the both data, whereby the counter 110 outputs address data "4". At a subsequent time $t_{n+3}$, the flip-flops $P_1$ to $P_5$ latch data as shown at FIG. 30($b$), which are also mismatched with data ($D_4$ to $D_0$) of an address "4" as shown in FIG. 28. Thus, the counter 110 is continuously preset at "4". Thus, the pattern of FIG. 28 is not recognized with respect to the inspection surface having the pattern as shown in FIG. 29.

In order to avoid the aforementioned problem, therefore, the flip-flops $P_6$ to $P_{20}$ and the selector 106 are provided as shown at FIG. 20 to also precedingly check pattern matching in the time-series direction. The reason for this is as follows: It is assumed here that the memory 105 stores memory data as shown in FIG. 31 and an inspected surface has the pattern as shown in FIG. 29. At the time $t_{n-1}$, the flip-flops $P_{11}$ to $P_{15}$ latch data as shown at FIG. 32($a$). Since the counter 110 is preset at "5" at this time, the selector 106 selects the flip-flops $P_{11}$ to $P_{15}$. As the result, the exclusive OR circuits XOR1 to XOR5 compare the data of FIG. 32($a$) with data ($D_4$ to $D_0$) of an address "5" as shown in FIG. 31. Since these data are not matched with each other, "5" is continuously preset at the counter 110.

At the subsequent time $t_n$, the flip-flops $P_{11}$ to $P_{15}$ latch data as shown at FIG. 32($b$). Since the selector 106 continuously selects the flip-flops $P_{11}$ to $P_{15}$ at this time, the data of FIG. 32($b$) are compared with data ($D_4$ to $D_0$) of an address "5" as shown in FIG. 31. Since these data are matched with each other, the counter 110 is subtracted to output the data of the address "4".

When the data of the address "4" are thus outputted, the selector 106 is switched from the flip-flops $P_{11}$ to $P_{15}$ to the flip-flops $P_1$ to $P_5$ at the subsequent time $t_{n+1}$. Therefore, the inspected object image data in the subdirection latched by the flip-flops $P_1$ to $P_5$ are thereafter sequentially compared with the first standard image data stored in addresses "4" to "0" of the memory 105, to perform pattern recognition. Thus, the pattern corresponding to the lines or line width as shown in FIG. 29 can also be correctly recognized.

Pattern Example 3

Figure 33A:
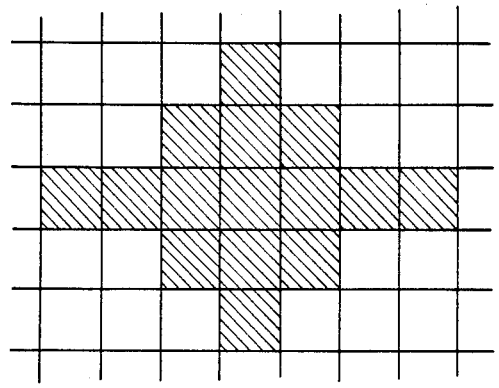
FIG. 33A illustrates a pattern on an inspected surface.
Figure 33B:
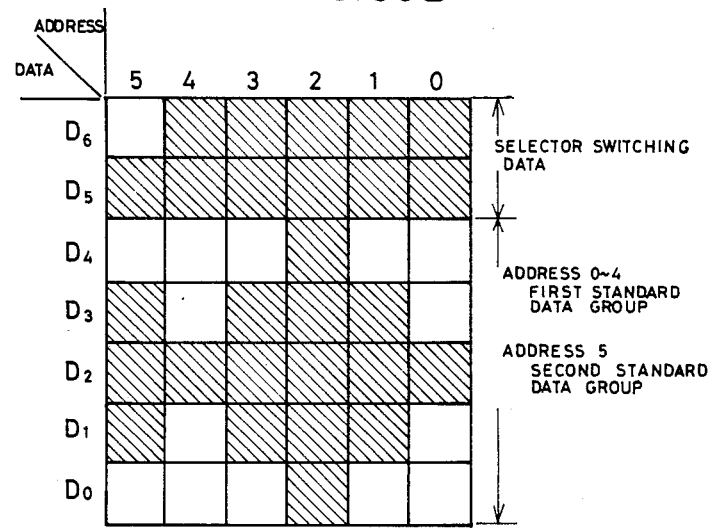
FIGS. 33B and 34 illustrate memory data stored in a memory.

The flip-flops for precedingly checking pattern matching in the time-series direction are provided in a plurality of trains (trains $P_6$ to $P_{10}$, $P_{11}$ to $P_{15}$ and $P_{16}$ to $P_{20}$ in this embodiment) as shown in FIG. 20 for the following reason: When recognition is made as to whether or not the pattern as shown in FIG. 21 is present with respect to a pattern as shown at FIG. 33A whose central portion is extended in the time-series direction, a pattern recognition error may be caused even if pattern matching in the time-series direction is precedingly checked by the central train of flip-flops $P_{11}$ to $P_{15}$. However, the flip-flops are provided in a plurality of trains as hereinabove described to make selector switching data $D_6$ and $D_5$ of the address "5" stored in the memory 105 selectively switched to any flip-flop train as shown at FIG. 33B, to enable correct pattern recognition by selecting either the flip-flop train $P_6$ to $P_{10}$ or $P_{16}$ to $P_{20}$ by the selector 106 to check pattern matching in the time-series direction even if the pattern as shown in FIG. 33A is recognized. In this case, the address "5" stored in the memory 105 stores, in addition to the selector switching data ($D_6$ and $D_5$), the following image data as standard image data ($D_4$ to $D_0$): Namely, the address "5" stores standard image data in a main scanning direction train corresponding to the flip-flop train selected by the selector 106 within the first standard image group as shown at FIG. 33B.

Pattern Example 4

Figure 34:
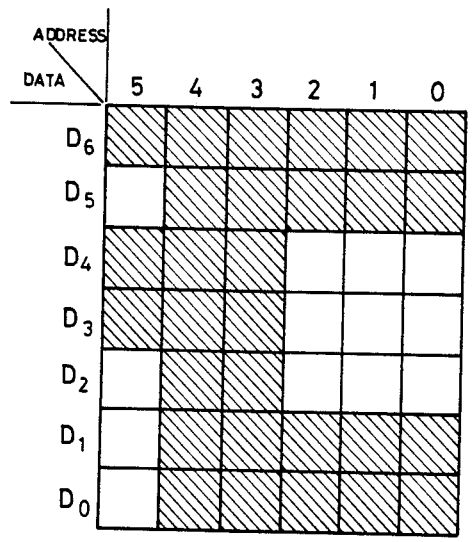
Figure 35:
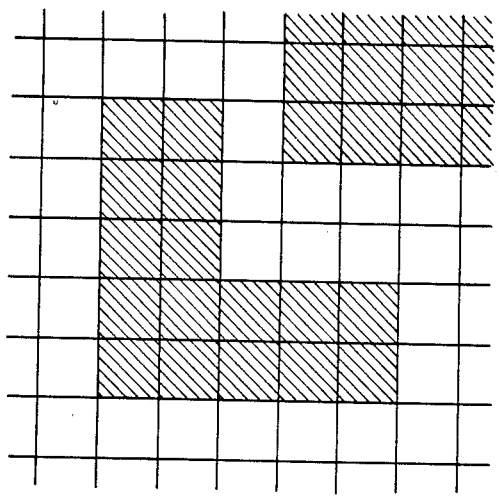
FIGS. 35 and 36 illustrate patterns on inspected surfaces.
Figures 36, 37:
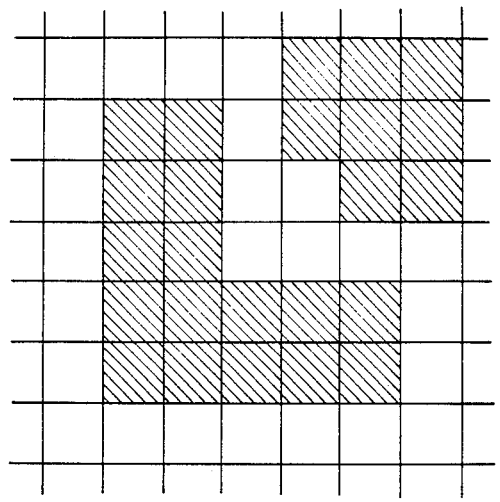
FIG. 37 illustrates masking data stored in a memory.

Description is now made on the function of the memory 107. For convenience of illustration, it is assumed here that recognition is made on an L-shaped pattern defined by data ($D_4$ to $D_0$) of addresses "0" to "4" as shown in FIG. 34. Further, it is assumed that other patterns are present in the vicinity of the L-shaped pattern on the inspected surface as shown in FIGS. 35 and 36. If all of the addresses of the memory 107 are written with "1" as hereinabove described with reference to the preceding example, the data sequentially outputted from the flip-flops $P_1$ to $P_5$ are matched with the data ($D_4$ to $D_0$) sequentially outputted from the memory 105 in memory addresses "4" to "2", while no such matching is obtained in case of memory addresses "1" and "0". Therefore, the aforementioned L-shaped pattern is not recognized.

However, recognition of the L-shaped pattern is enabled by storing such masking data as shown in FIG. 37 in the memory 107. When the data ($D_4$ to $D_0$) of the address "1" of the memory 105 are compared, the exclusive OR circuit XOR1 outputs "1" with respect to the patterns of FIGS. 35 and 36 and the other exclusive OR circuits XOR2 to XOR5 output "0". However, the AND circuit AND1 outputs "0" by masking data ($D_4$ to $D_0$) of the address "1" in FIG. 37 outputted from the memory 107. As the result, all of the AND circuits AND1 to AND5 output "0" and the OR circuit 108 outputs "0", whereby pattern matching is recognized in a required portion. Similarly, when the data ($D_4$ to $D_0$) of the address "0" in FIG. 34 of the memory 105 are compared, the exclusive OR circuit XOR1 outputs "1" with respect to the pattern of FIG. 35 and the exclusive OR circuits XOR1 and XOR2 output "1" with respect to the pattern of FIG. 36. However, both of the AND circuits AND1 and AND2 output "0" by the masking data ($D_4$ to $D_0$) of the address "0" in FIG. 37 outputted from the memory 107. Namely, pattern matching in a necessary portion is also recognized in this case. A series of pattern recognition is performed in such a manner, whereby the L-shaped pattern as shown in FIG. 35 is recognized in a timing chart similar to that shown in FIG. 24.

Pattern Example 5

Figure 38:
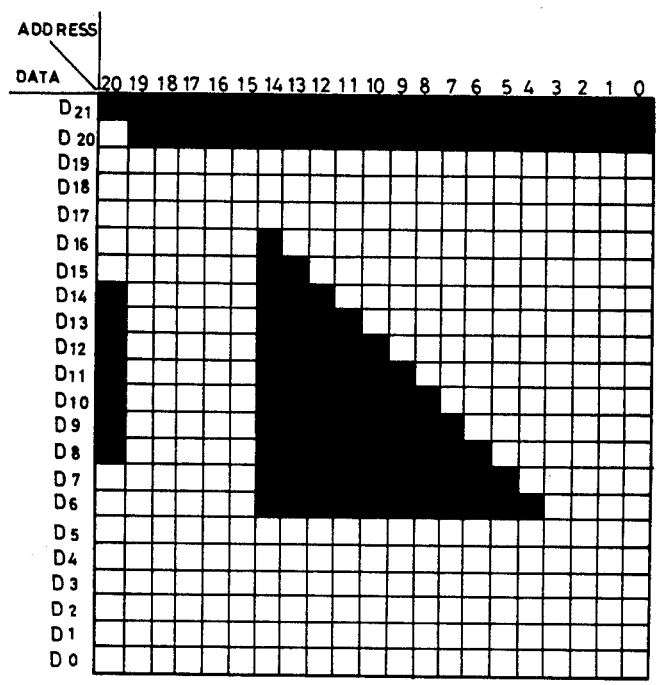
FIG. 38 illustrates memory data stored in a memory.
Figure 39:
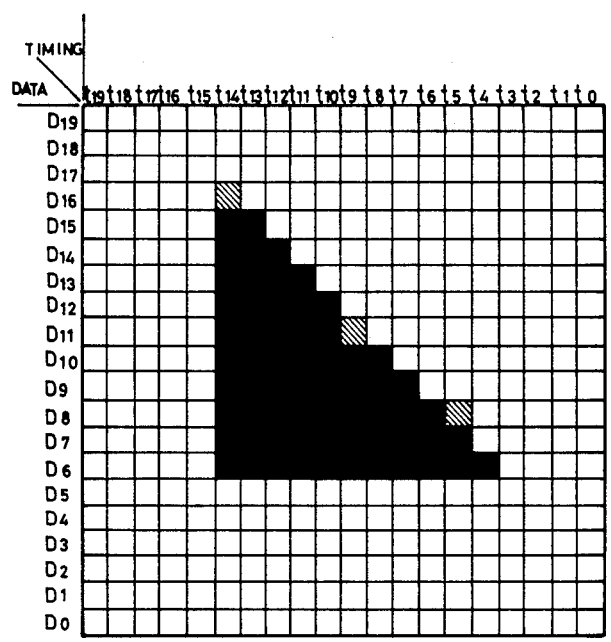
FIG. 39 illustrates image data including quantization errors inputted through an input device.
Figure 40:
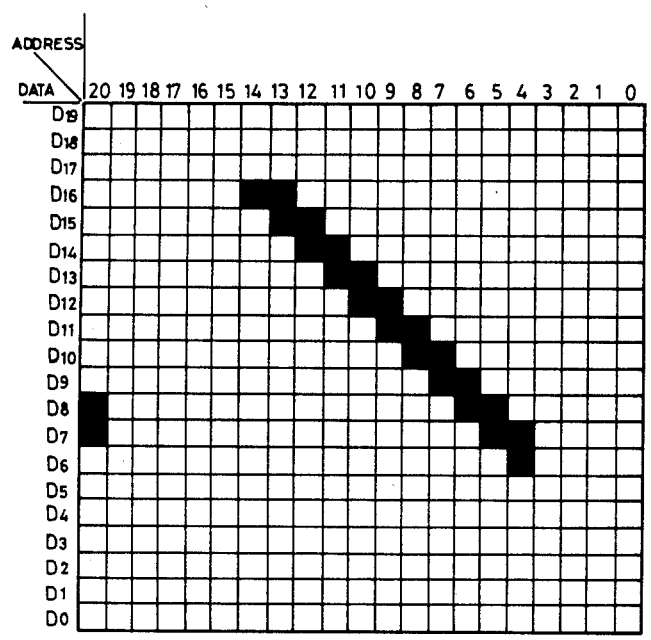
FIG. 40 illustrates masking data stored in a memory.

Description is now made on another function of the memory 107. Generally when a definite pattern on the inspected object 101 is inputted by the input device 102, data uncertain portions following quantization errors may be caused in boundary portions or the like by optical system problems or problems in the scanning position, whereby image data slightly different from the actual pattern are obtained. Also in this case, pattern recognition can be performed in a state identical to that with no quantization error by storing masking data for masking the said uncertain portions in the memory 107. Description is now made on the reason therefor with reference to the case of 20×20 pixel size, since appropriate expression is difficult with reference to 5×5 pixel size. It is assumed here that pattern recognition as shown in a range of addresses "0" to "19" and data $D_0$ to $D_{19}$ as shown in FIG. 38 is to be performed. Generally when such a pattern is inputted by the input device 102, image data including quantization errors such as $t_{14}$-$D_{16}$, $T_9$-$D_{11}$ and $T_5$-$D_8$ are obtained in boundary portions for example, as shown by slant lines in FIG. 39. Such quantization errors can be disregarded to preform pattern recognition by storing masking data having data of "0" in regions corresponding to the boundary portions as shown in FIG. 40.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pattern masking method for masking through-hole patterns comprising:
   an image data creating step of inputting binarized image data of an inspected object having through-holes in a time-series manner along a main scanning direction to sequentially create a binarized image data group for a plurality of pixels arrayed in a sub-scanning direction;
   a pattern discriminating step of judging whether of not the pattern of an inputted image corresponds to a standard through-hole pattern on the basis of said sequentially created binarized image data group, said pattern discriminating step including:
   a diameter measuring step of measuring through-hole diameters on the basis of through-hole data continuous from a central pixel position of said binarized image data group created in said image data creating step along the sub-scanning direction,
   an area judging step of calculating a through-hole area by sequentially cumulatively adding said measured through-hole diameters in order along the main scanning direction and comparing said calculated through-hole area with maximum and minimum allowable area values to judge whether or not said through-hole area is included in an allowable range, and
   a diameter judging step of comparing measured through-hole diameters sequentially with maximum and minimum allowable diameters in order along the main scanning direction when said calculated through-hole area is judged to be within said allowable range to judge whether or nor said measured through-hole diameters are included in said allowable range, thereby to judge that said pattern of said inputted image corresponds to said standard through-hole pattern when a determination is made that all of said measured through-hole diameters are within said allowable range;
   a masking data creating step of sequentially creating through-hole diameter masking data, in order, along the main scanning direction when said pattern of said inputted image is judged to correspond to said standard through-hole pattern, said masking data creating step including a step of creating through-hole diameter masking data identical in diameter with said measured through-hole diameters; and
   a masking processing step of sequentially performing masking processing on said binarized image data group of said inspected object arrayed in the sub-scanning direction on the basis of said through-hole masking data.

2. A pattern masking method for masking through-hole patterns comprising:
   an image data creating step of inputting binarized image data of an inspected object having through-holes in a time-series manner along a main scanning direction to sequentially create a binarized image data group for a plurality of pixels arrayed in a sub-scanning direction;
   a pattern discriminating step of judging whether of not the pattern of an inputted image corresponds to a standard through-hole pattern on the basis of said sequentially created binarized image data group, said pattern discriminating step including:
   a diameter measuring step of measuring through-hole diameters on the basis of through-hole data continuous from a central pixel position of said binarized image data group created in said image data creating step along the sub-scanning direction,
   An area judging step of calculating a through-hole area by sequentially cumulatively adding said measured through-hole diameters in order along the main scanning direction and comparing said calculated through-hole area with maximum and minimum allowable area values to judge whether or not said through-hole area is included in an allowable range, and
   a diameter judging step of comparing measured through-hole diameters sequentially with maximum and minimum allowable diameters in order along the main scanning direction when said calculated through-hole area is judged to be within said allowable range to judge whether or nor said measured through-hole diameters are included in an allowable range, thereby to judge that said pattern of said inputted image corresponds to said standard through-hole pattern when a determination is made that all of said measured through-hole diameters are within said allowable range;
   a masking data creating step of sequentially creating through-hole diameter masking data in order along the main scanning direction when said pattern of said inputted image is judged to correspond to said standard through-hole pattern, said masking data creating step including a step of creating through-hole diameter masking data by adding a required size to said measured through-hole diameters; and a masking processing step of sequentially performing masking processing on said binarized image data group of said inspected object arrayed in the sub-scanning direction on the basis of said through-hole masking data.

3. A pattern masking method for masking through-hole patterns comprising:

an image data creating step of inputting binarized image data of an inspected object having through-holes in a time-series manner along a main scanning direction to sequentially create a binarized image data group for a plurality of pixels arrayed in a sub-scanning direction;

a pattern discriminating step of judging whether the pattern of an inputted image corresponds to a standard through-hole pattern on the basis of said sequentially created binarized image data group, said pattern discriminating step including:

a diameter measuring step of measuring through-hole diameters on the basis of through-hole data continuous from a central pixel position of said binarized image data group created in said image data creating step along the sub-scanning direction, an area judging step of calculating a through-hole area by sequentially cumulatively adding said measured through-hole diameters, in order, along the main scanning direction and comparing said calculated through-hole area with maximum and minimum allowable area values to judge whether or not said through-hole area is included in an allowable range, and a diameter judging step of comparing measured through-hole diameters sequentially with maximum and minimum allowable diameters in order along the main scanning direction when said calculated through-hole area is judged to be within said allowable range to judge whether or nore* said measured through hole diameters are included in an allowable range, thereby to judge that said pattern of said inputted image corresponds to said standard through-hole pattern when a determination is made that all of said measured through-hole diameters are within said allowable range;

a masking data creating step of sequentially creating through-hole diameter masking data, in order, along the main scanning direction when said pattern of said inputted image is judged to correspond to said standard through-hole pattern, said masking data creating step including a step of creating through-hole diameter masking data of a prescribed diameter larger than said actual through-hole diameters; and a masking processing step of sequentially performing masking processing on said binarized image data group of said inspected object arrayed in the sub-scanning direction on the basis of said through-hole masking data.

4. A pattern masking method for masking through-hole patterns comprising:

an image data creating step of inputting binarized image data of an inspected object having through-holes in a time-series manner along a main scanning direction to sequentially create a binarized image data group for a plurality of pixels arrayed in a sub-scanning direction;

a pattern discriminating step of judging whether the pattern of an inputted image corresponds to a standard through-hole pattern on the basis of said sequentially created binarized image data group, said pattern discriminating step including:

a storing step of storing binarized image data of said standard through-hole pattern by m pixels (m: integer larger than 2) in the sub-scanning direction and n pixels (n: integer larger than 2) in the main scanning direction in a memory as a first image data group, a comparing step of comparing an inspected image data group for m pixels created in said image data creating step with said standard image data group for m pixels in the sub-scanning direction selectively read from said memory per corresponding pixel, and a data reading step of incrementing a counter when all groups of pixels are matched in said comparing step while resetting said counter when at least a group of pixels are mismatched so as to read from said memory said standard binarized image data group for m pixels in the sub-scanning direction in response to incrementing of said counter in a time-series manner along the main scanning direction, thereby to make comparison with said inspected binarized image data group, thereby to judge that said pattern of said inputted image corresponds to said standard through-hole pattern when incrementing of said counter continues n times;

a masking data creating step of sequentially creating through-hole diameter masking data in order along the main scanning direction when said pattern of said inputted image is judged to correspond to said standard through-hole pattern; and a masking processing step of sequentially performing masking processing on said binarized image data group of said inspected object arrayed in the sub-scanning direction on the basis of said through-hole diameter masking data.

5. A pattern masking apparatus for masking through-hole patterns, comprising:

image data creating means for inputting binarized image data of an inspected object having through-holes in a time-series manner to sequentially create a binarized image data group for a plurality of pixels arrayed in a sub-scanning direction;

pattern discriminating means for judging whether the pattern of an inputted image corresponds to a standard through-hole pattern on the basis of said sequentially created binarized image data group;

masking data creating means for sequentially creating through-hole diameter masking data, in order, along a main scanning direction when said pattern of said inputted image is judged to correspond to said standard through-hole pattern, said diameter judging means i including:

a pattern data memory storing maximum and minimum allowable through-hole diameter data of said standard through-hole arrayed in order along the main scanning direction in order of addresses with jumped addresses being as head addresses, a first delay circuit for delaying through-hole diameter data measured by said diameter measuring means by prescribed pixels, second data reading means for reading data stored in said pattern data memory synchronously with the delay by said first delay circuit in order to addresses from said jumped addresses, and a diameter judging circuit for sequentially comparing said measured through-hole diameter data outputted from said first delay circuit with said maximum and minimum allowable through-hole data read from said pattern data memory to output a pattern matching signal when all of said measured through-hole diameter data are within an allowable range; and masking processing means for sequentially performing masking processing on said binarized image data group of said inspected object arrayed in the sub-scanning direction on the basis of said through-hole diameter masking data, said pattern discriminating means including diameter measuring means for measuring through-hole diameters on the basis of through-hole data continuous from a central pixel position of said binarized image data group created in said image data creating means along the sub-scanning direction, area judging means for calculating a through-hole area by sequentially cumulatively adding measured through-hole diameters, in order, along the main scanning direction and comparing said calculated through-hole area with maximum and minimum allowable area values to judge whether or not said calculated through-hole area is included in an allowable range, and diameter judging means for sequentially comparing measuring through-hole diameters with maximum and minimum allowable diameters in order along the main scanning direction when said calculated through-hole area is judged to be within said allowable range to judge whether said measured through-hole diameters are included in an allowable range, thereby to determine that said pattern of said inputted image corresponds to a through-hole when all of said actual through-hole diameters are judged to be within said allowable range.

6. A pattern masking apparatus for masking through-hole patterns, comprising:

image data creating means for inputting binarized image data of an inspected object having through-holes in a time-series manner along a main scanning direction to sequentially create a binarized image data group for a plurality of pixels arrayed in a sub-scanning direction;

pattern discriminating means for measuring through-hole diameters in the sub-scanning direction on the basis of said sequentially created binarized image data group, for comparing sequentially measured through-hole diameters with predetermined maximum and minimum allowable diameters respectively, in order, along the main scanning direction to determine whether or not the pattern of an inputted image corresponds to a standard through-hole pattern, said pattern discriminating means comprising:

a memory storing binarized data of said standard through-hole pattern by m pixels (m: integer larger than 2) in the sub-scanning direction and by n pixels (n: integer larger than 2) in the main scanning direction as a first standard group, a comparator for comparing a first inspected image data group for m pixels created by said image data creating means with a standard image data group by m pixels in the sub-scanning direction selectively called from said memory per corresponding pixel to output a matching signal when all of groups of pixels are matched with each other while outputting a mismatch signal when at least a group of pixels are mismatched, and a pattern judging circuit for inputting an output signal from said comparator in a counter to step said counter when said matching signal is inputted while presetting said counter when said mismatch signal is inputted to call said standard image data group for m pixels in the sub-scanning direction stored in said memory in a time-series manner along the main scanning direction in response to stepping of said counter to make the same compared with said first inspected image data group, thereby to output a pattern matching signal when said counter stepping continues n times;

masking data creating means for sequentially creating through-hole diameter masking data, in order, along the main scanning direction when said pattern of said inputting image is judged to correspond to said standard through-hole pattern; and masking processing means for sequentially performing masking processing on said binarized image data group of said inspected object arrayed in the sub-scanning direction on the basis of said through-hole diameter masking data.

7. A pattern masking apparatus in accordance with claim 6, further comprising a selector;

said image data creating means latching a second inspected image data group in the main scanning direction arrayed in a time-series manner in a front stage side in correspondence to any one of image data included in said first standard image data group;

said memory storing said second standard image data group as image data in main scanning direction columns corresponding to said second inspected image data group while further storing selector switching data;

said selector inputting said second inspected image data group in said comparator on the basis of said selector switching data to make the same compared with said second standard image data group when said counter is preset by inputting said mismatch signal while inputting said first inspected image data group in said comparator on the basis of said selector switching data to make the same compared with said first standard image data group when said counter is stepped by inputting said matching signal.

8. A pattern masking apparatus in accordance with claim 7, wherein said image data creating means latches a plurality of columns of said second inspected image data groups, and said selector selectively inputs any one of inspected image data group in said plurality of second inspected image data groups in said comparator on the basis of said selector switching data to make the same compared with said second standard image data group when said counter is preset.

9. A pattern masking apparatus in accordance with claim 6, wherein said comparator includes means of masking results of comparison of specific pixels of said first inspected image data group and said first standard image data group.

* * * * *